United States Patent
Lauer

(10) Patent No.: US 9,061,129 B2
(45) Date of Patent: Jun. 23, 2015

(54) MEDICAL PORT, BLOOD HOSE FOR USE IN AN EXTRACORPOREAL BLOOD TREATMENT AS WELL AS MEDICAL TREATMENT APPRATUS

(75) Inventor: Martin Lauer, St. Wendel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 322 days.

(21) Appl. No.: 13/559,710

(22) Filed: Jul. 27, 2012

(65) Prior Publication Data

US 2013/0030348 A1     Jan. 31, 2013

Related U.S. Application Data

(60) Provisional application No. 61/512,946, filed on Jul. 29, 2011.

(30) Foreign Application Priority Data

Jul. 29, 2011   (DE) .......................... 10 2011 108 787

(51) Int. Cl.
| | |
|---|---|
| *A61M 5/00* | (2006.01) |
| *A61M 39/22* | (2006.01) |
| *A61M 5/14* | (2006.01) |
| *A61M 5/168* | (2006.01) |
| *A61M 39/02* | (2006.01) |

(Continued)

(52) U.S. Cl.
CPC ........... *A61M 39/223* (2013.01); *A61M 5/1407* (2013.01); *A61M 5/16827* (2013.01); *A61M 39/02* (2013.01); *A61M 2039/0036* (2013.01); *A61M 2039/1072* (2013.01); *A61M 2039/229* (2013.01); *F16K 11/0853* (2013.01)

(58) Field of Classification Search
CPC . A61M 39/00; A61M 39/10; A61M 2039/00; A61M 1/14; A61M 2039/229; A61M 5/16827; F16K 37/00
USPC ............ 251/283, 309, 314, 304; 137/625.46, 137/625.47; 604/9
See application file for complete search history.

(56) References Cited

U.S. PATENT DOCUMENTS 4,230,128 A   10/1980   Aramayo
4,951,661 A   8/1990    Sladek (Continued)

FOREIGN PATENT DOCUMENTS

| EP | 1234596 A1 | 8/2002 | |
|---|---|---|---|
| EP | 1555041 | * 7/2005 | ............ A61M 39/02 |

(Continued)

*Primary Examiner* — Leslie Deak
*Assistant Examiner* — Kai Weng
(74) *Attorney, Agent, or Firm* — Kenyon & Kenyon LLP

(57) ABSTRACT

A medical port includes a main channel with a lumen to conduct a first fluid through the port, a secondary channel aperture of a secondary channel to add a second fluid in the main channel, at least one housing element and at least one actuation element arranged to be transferable relative to the housing element from a first position into a second position, a seal section, which is arranged to be rotatable between a first position of the seal section, in which the seal section does not close, seal or cover the secondary channel aperture and a second position of the seal section, in which the seal section closes, seals or covers the secondary channel aperture, when the actuation element is transferred from the first position to the second position. A blood hose including at least one port, and a medical treatment apparatus are also described.

20 Claims, 29 Drawing Sheets

(51) Int. Cl.
*F16K 11/085* (2006.01)
*A61M 39/00* (2006.01)
*A61M 39/10* (2006.01)

(56) References Cited

U.S. PATENT DOCUMENTS 5,135,026 A    8/1992   Manska

2004/0210162 A1    10/2004   Wyatt et al.
2010/0319796 A1*   12/2010   Whitaker ................. 137/625.46

FOREIGN PATENT DOCUMENTS

| EP | 1555041 A1 | 7/2005 |
| EP | 1 627 658 B1 | 3/2012 |
| WO | 2011-143049 A2 | 11/2011 |

* cited by examiner

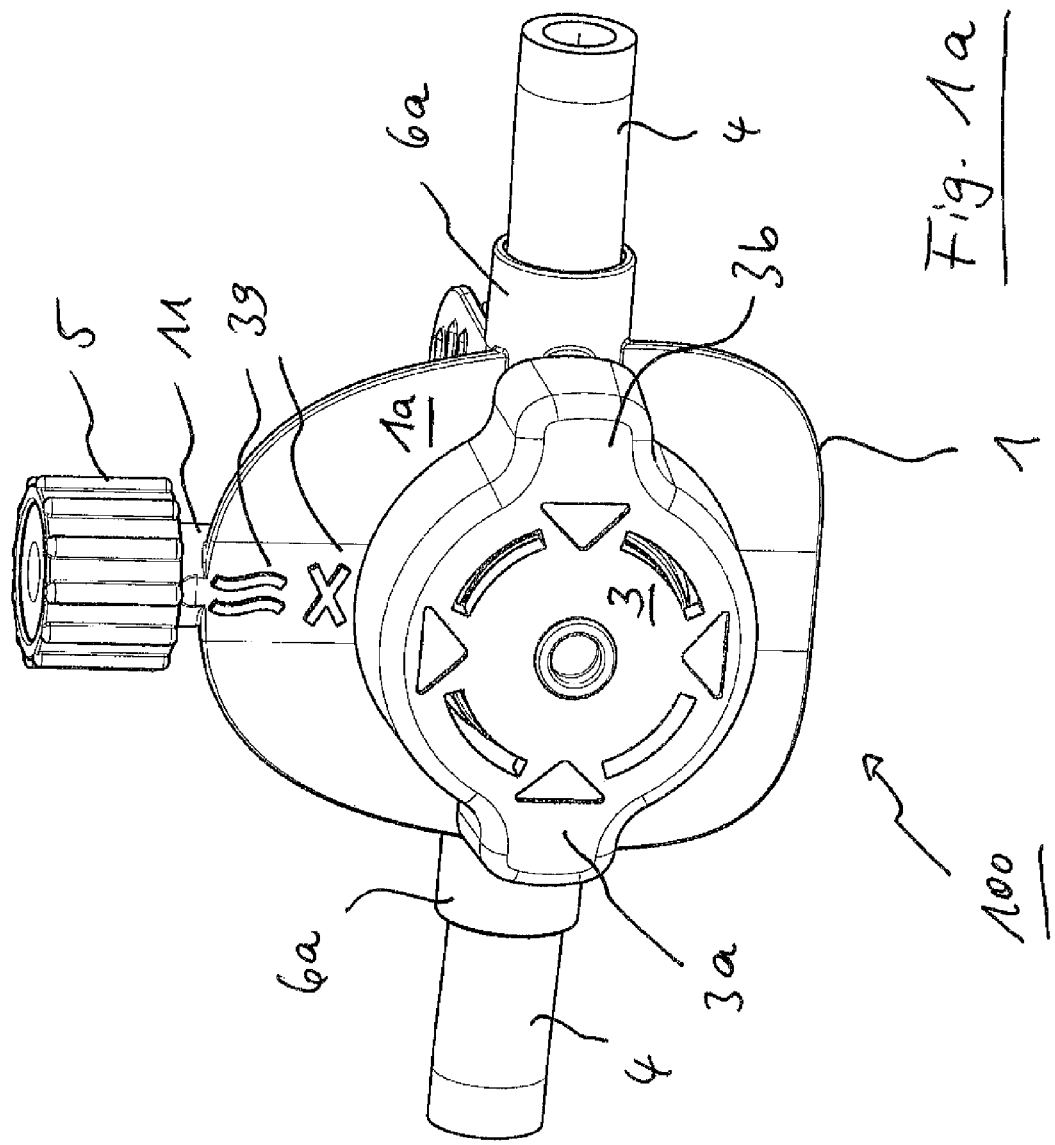

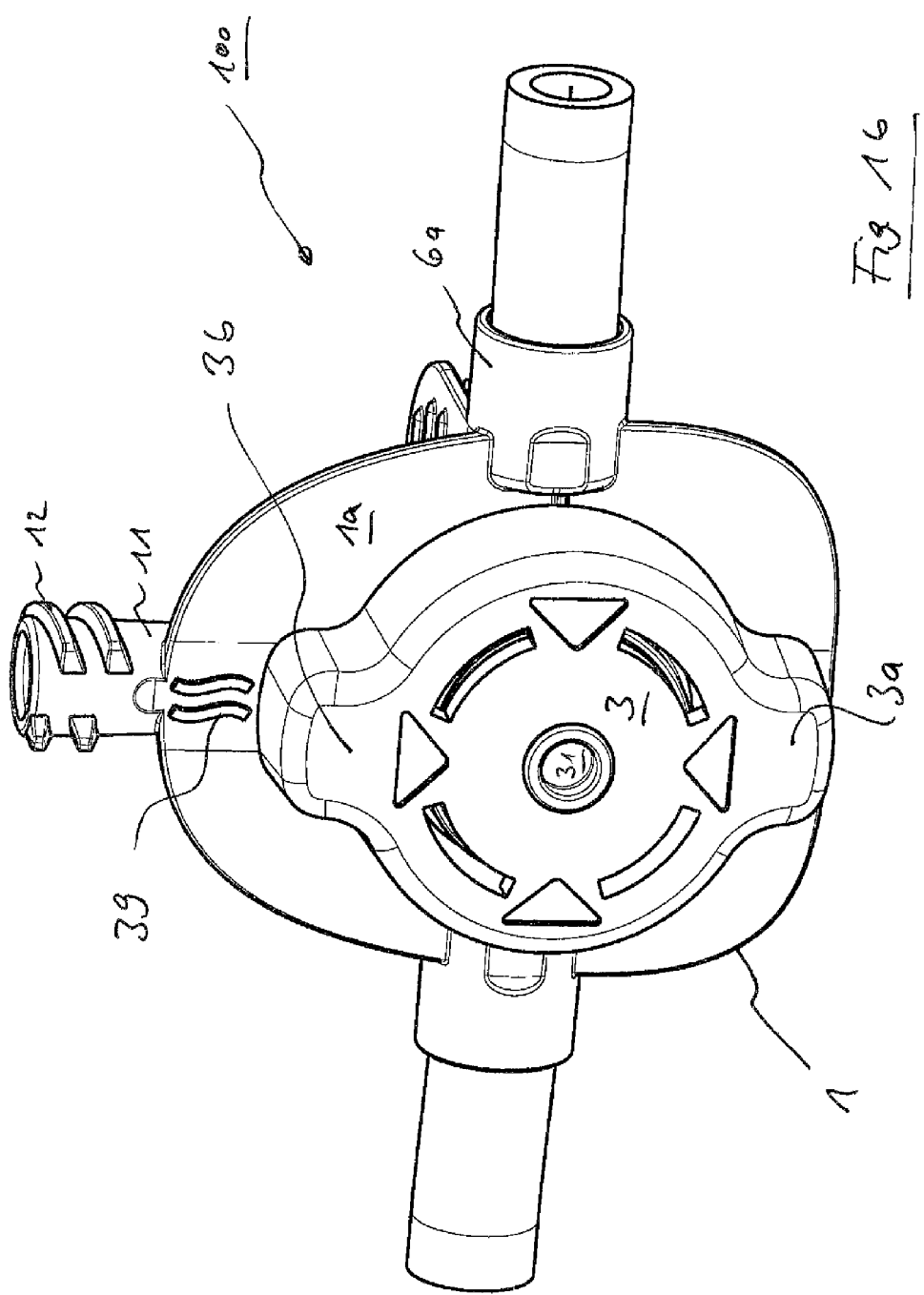

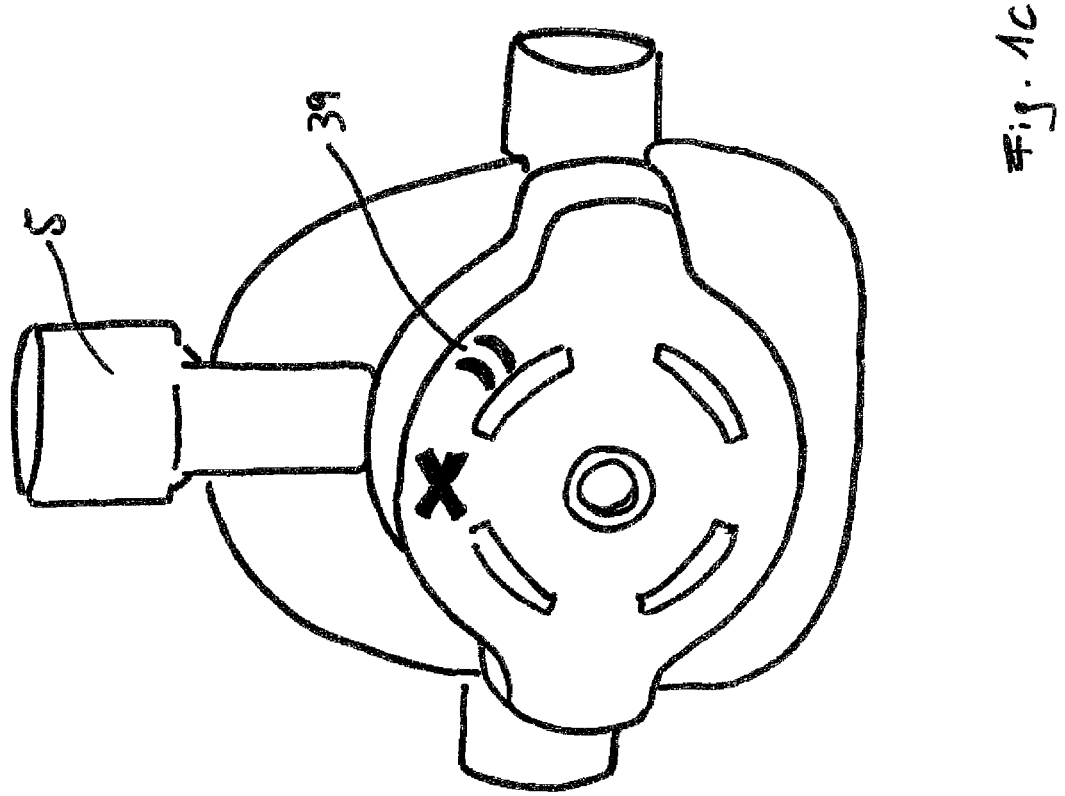

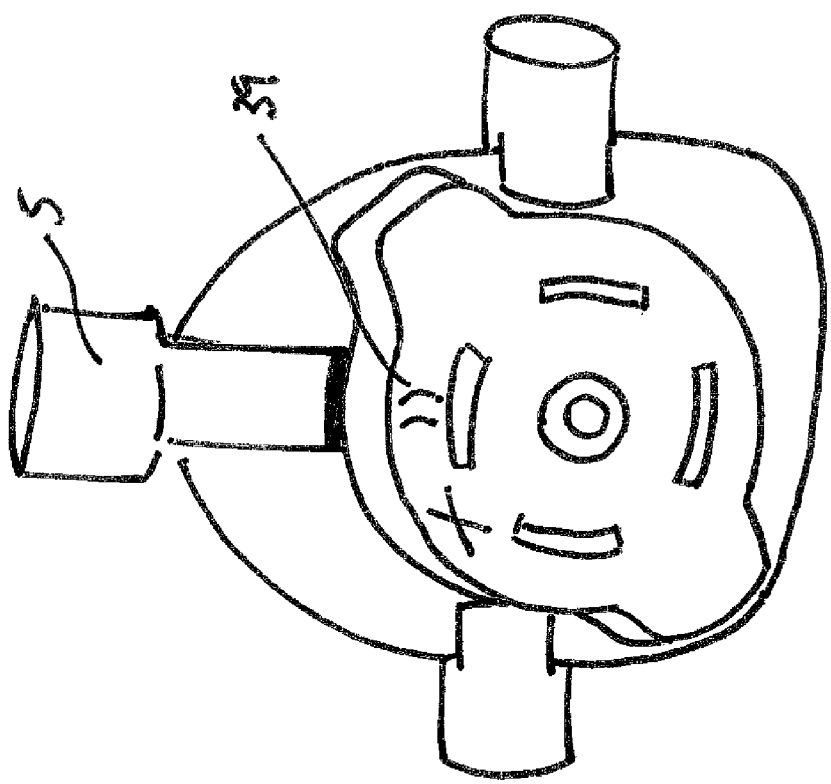

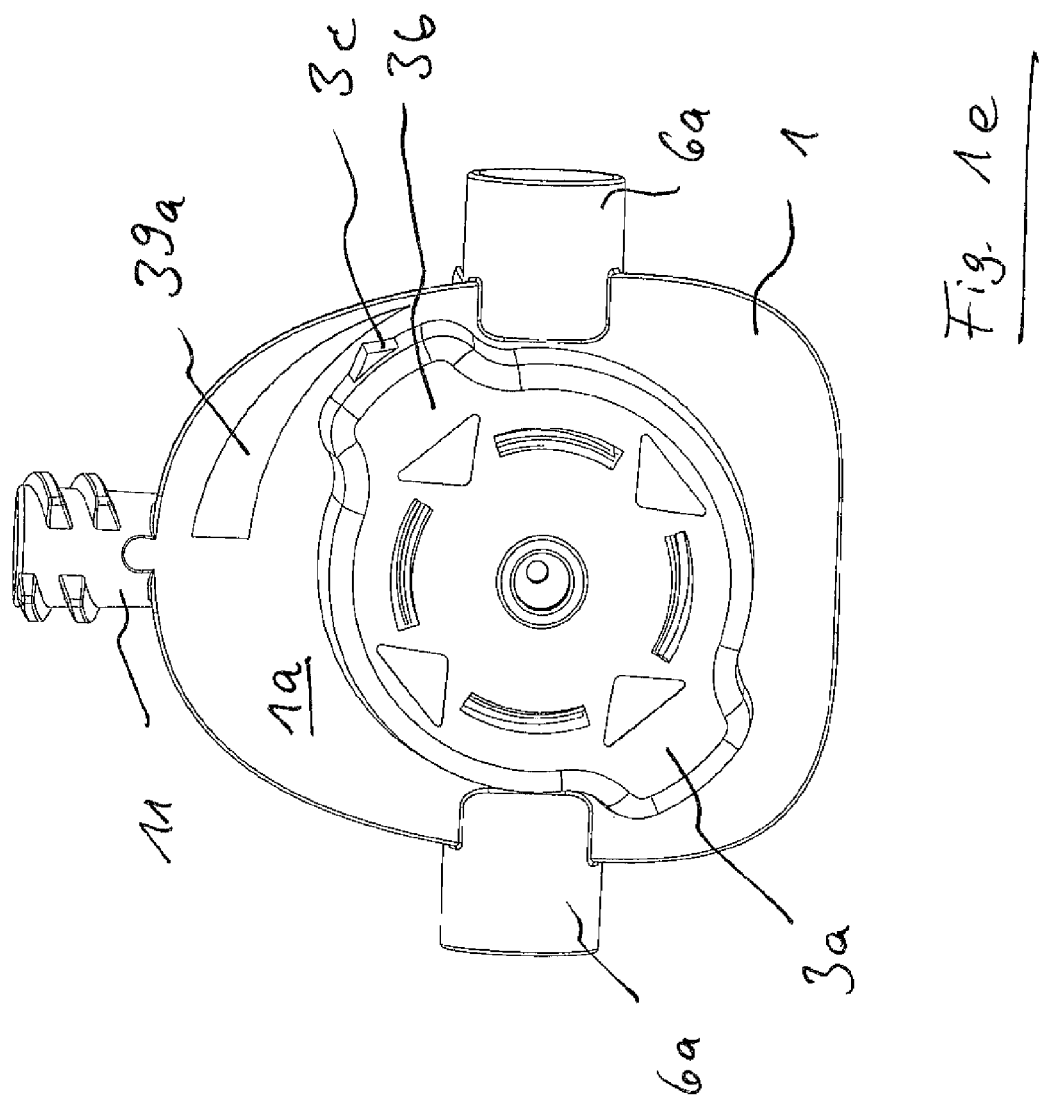

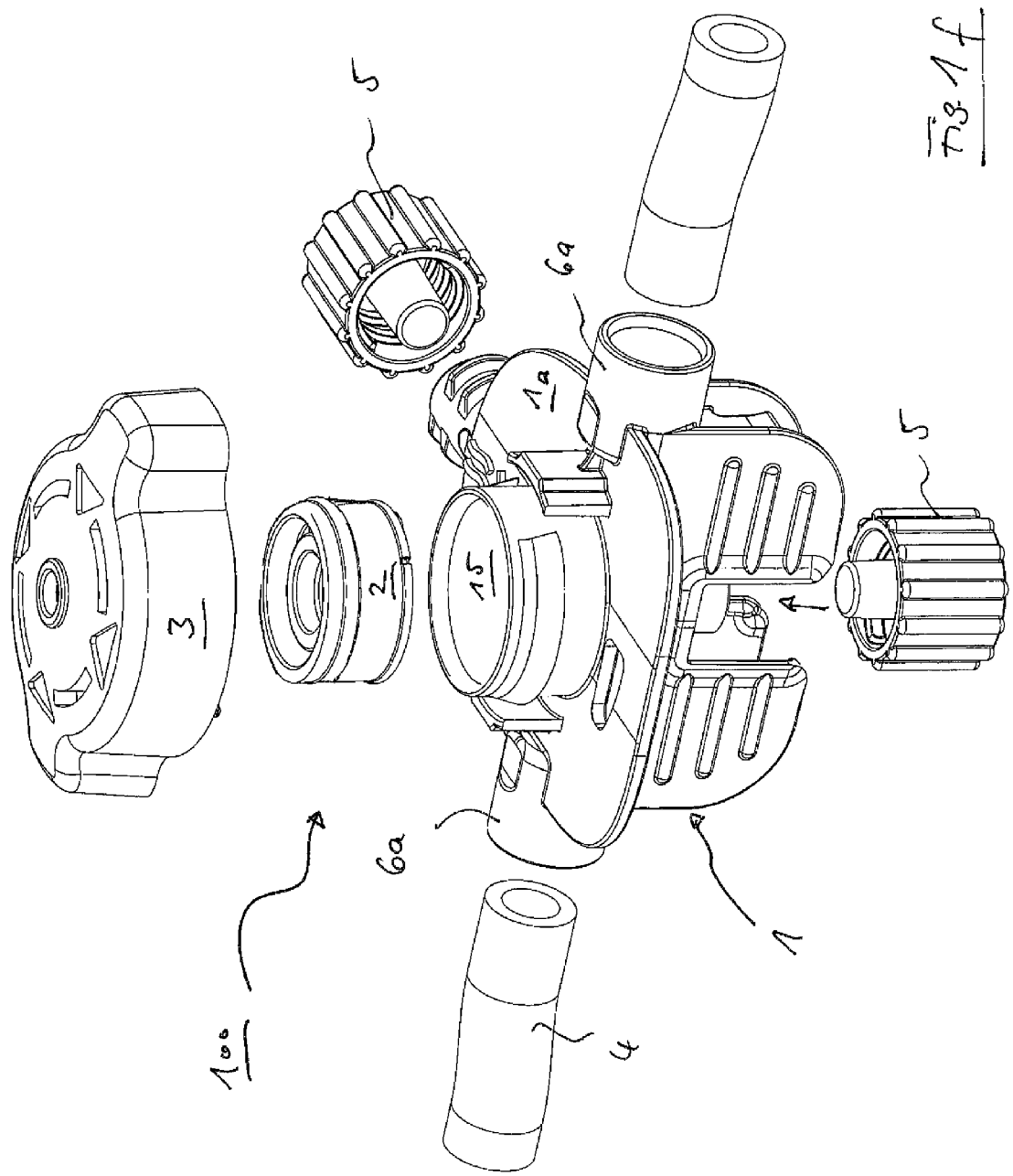

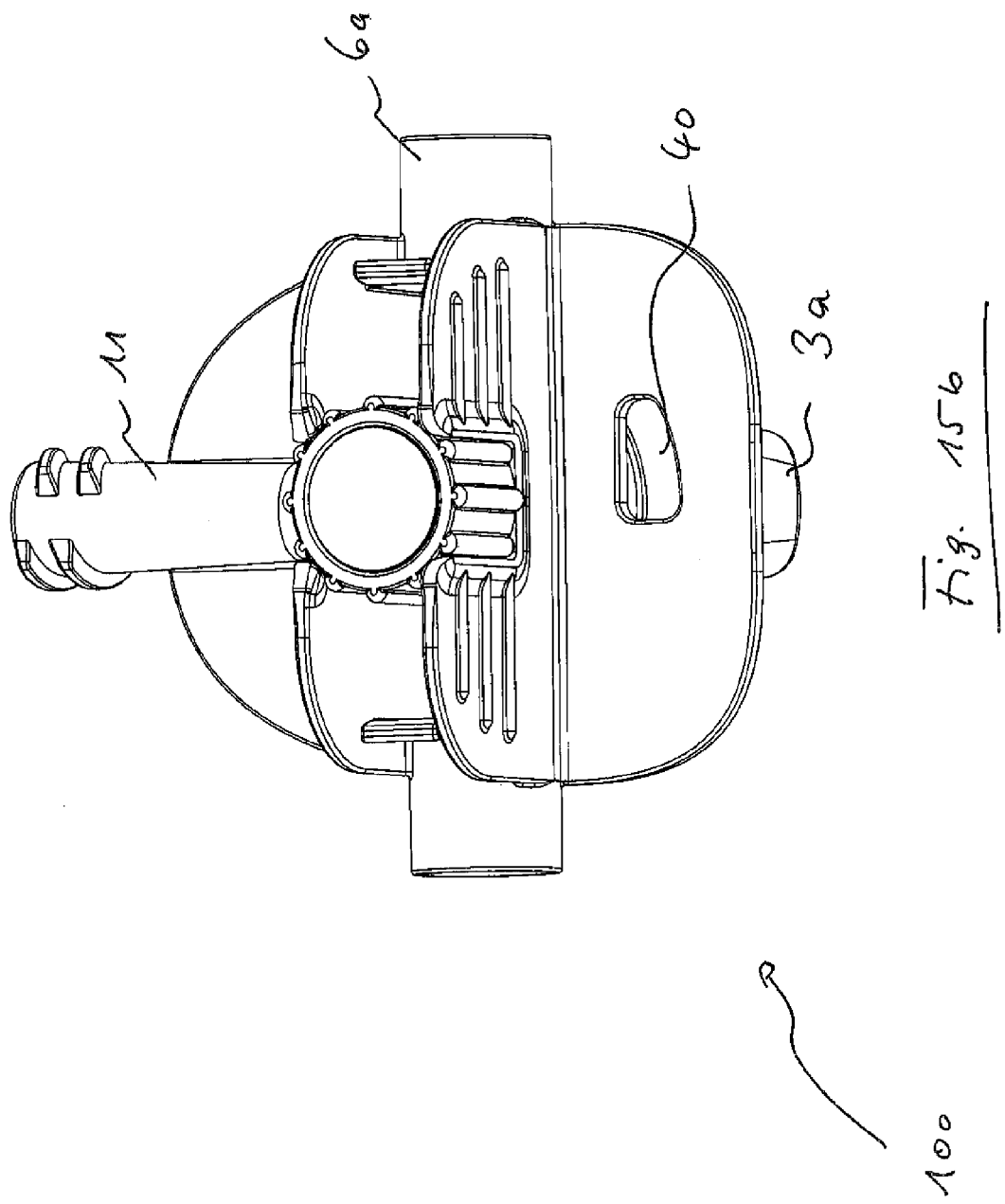

MEDICAL PORT, BLOOD HOSE FOR USE IN AN EXTRACORPOREAL BLOOD TREATMENT AS WELL AS MEDICAL TREATMENT APPRATUS

CROSS-REFERENCES TO RELATED APPLICATIONS

The present application claims priority to U.S. Provisional Application No. 61/512,946, filed on Jul. 29, 2011, and claims priority to Application No. DE 10 2011 108 787.0, filed in the Federal Republic of Germany on Jul. 29, 2011, each of which is expressly incorporated herein in its entirety by reference thereto.

FIELD OF INVENTION

The present invention relates to a medical port. It further relates to a blood hose and a medical treatment apparatus.

BACKGROUND INFORMATION

When using medical treatment apparatuses, as in the area of laboratory analysis equipment, fluid systems with hoses, connectors, bags, pumps, chambers etc. are frequently used. Thereby, regularly a first fluid flowing through a main channel of the fluid system, usually a liquid, for example blood, dialysis fluid or infusion solution, is sampled. Likewise it is common to dose a second fluid, for example a treatment liquid, a medication or similar into the first fluid. Both cases demand reclosable access points in the fluid system, which are in practice commonly called "ports."

SUMMARY

One object of the present invention is to describe a further medical port. In addition, a blood tube or hose for use in an extracorporeal blood treatment as well as a medical treatment apparatus are described.

In all of the following exemplary embodiments, the use of the expressions "hose," "hose section," "hose clamp," etc. is understood to be synonymous with "tube," "tube section," "tube clamp," etc., respectively, according to exemplary embodiments of the present invention.

The port according to the present invention comprises a main channel with a lumen to conduct a first fluid through the port. The main channel comprises a secondary channel opening of a secondary channel for adding a second fluid into the main channel. In addition, the port comprises at least one housing element and at least one actuation element transferable from a first to a second position relative to the housing element. Furthermore, the port according to the present invention comprises a seal section which is arranged to be rotatable between a first position of the seal section in which the seal section does not close, seal or cover the secondary channel aperture (open position or valve position) and a second position of the seal section in which the seal section closes, seals or covers the secondary channel aperture (closed position or valve position), when the actuation element is transferred from one position to the other one.

The blood hose according to the present invention is suitable, intended and/or designed for being used in an extracorporeal blood treatment. Thereby, the blood hose comprises at least one port.

The medical treatment apparatus according to the present invention is connected with at least one blood hose according to the present invention.

Exemplary embodiments according to the present invention can comprise one or more of the features described herein, according to various exemplary embodiments according to the present invention.

In all of the following exemplary embodiments, the use of the expressions "can be" or "can have" etc. is understood to be synonymous with "is preferably" or respectively "has preferably" etc. and is intended to define exemplary embodiments according to the present invention.

The first fluid is in most cases a liquid, for example blood, dialysis liquid or infusion solution. The second fluid is regularly a treatment liquid, a medication or the like. The first as well as the second fluid can in addition be gases.

The main channel is in some exemplary embodiments according to the present invention integrated in the port according to the present invention in one piece.

In some exemplary embodiments according to the present invention, the main channel is embodied solely through the housing element, at least is located solely in this or is not extended out from this.

In some exemplary embodiments according to the present invention, the main channel does not extend into housings connected with the port.

In some exemplary embodiments according to the present invention, the transfer of the actuation element from one position to the other takes place by turning it, for example about its longitudinal axis.

In certain exemplary embodiments according to the present invention, the main channel of the port is a pipe.

In some exemplary embodiments according to the present invention, the main channel is embodied as a continuous and/or one-piece tube structure.

In some exemplary embodiments according to the present invention, the lumen of the main channel comprises no stepping relative to its longitudinal section.

In certain exemplary embodiments according to the present invention, the main channel comprises no alteration to its inner cross-section or its luminal cross-section. In other exemplary embodiments according to the present invention, the main channel comprises at most a continuous, but not one or more rapid or stepped alterations in its cross-section.

In some exemplary embodiments according to the present invention, the actuation element is transferred from its first position into its second position by turning, as is also the case in the exemplary embodiments according to the present invention which are explained in more detail with reference to the figures. The present invention is, however, not restricted to this. For example, the actuation element can also be actuated by means of a slide or push mechanism. But in any case the seal section twists between the herein named different positions during actuation of the actuation element.

In some exemplary embodiments of the port according to the present invention, the seal section is arranged and designed so that the passage of the first fluid through the main channel is impaired in neither its first nor its second position.

In certain exemplary embodiments of the port according to the present invention, the seal section is arranged and designed so that the passage of the first fluid through the main channel is impaired in neither its first nor its second position nor in any intermediate position between the first and the second position and/or during transition from the first to the second position.

In some exemplary embodiments according to the present invention any changing of the lumen or the cross section of the main channel and/or any influencing of fluid flowing or streaming through the main channel, e.g., its flow rate, the condition of its throttling and the like is understood as "impairing the passage."

Since impairing the passage can be accompanied by the generation or an increase of turbulences, preventing or avoiding impairing can be linked to advantages known to a person skilled in the art.

In some exemplary embodiments according to the present invention, the passage of the first fluid through the main channel is not changed through the transfer of the seal section from the first position to the second position (also designated as "closing the valve" herein).

The term "impair" is thereby in certain exemplary embodiments according to the present invention to be understood for example as to reduce, obstruct, derate, change the flow paths, and so on.

In some exemplary embodiments according to the present invention, in no position of the seal section is there a section of the seal section within the lumen of the main channel.

In some exemplary embodiments according to the present invention of the port, the main channel comprises, in addition to the secondary channel aperture, a septum aperture which during use of the port is sealed by means of a cannula pierceable septum.

In certain exemplary embodiments of the port according to the present invention a septum aperture is provided at the seal section, additionally to the secondary channel.

In some exemplary embodiments of the port according to the present invention the septum aperture or its main through passage direction is not arranged in parallel—but preferably essentially or completely perpendicular—to a main axial direction of the secondary channel.

In certain exemplary embodiments according to the present invention of the port, the secondary channel aperture and/or the septum aperture lead into a straight section of a cross-section of the lumen of the main channel or a segment or section thereof.

In some exemplary embodiments according to the present invention, a straight section is understood as a section of the main channel wall with an opening (for the secondary channel aperture or the septum aperture), which extends exclusively evenly or which is to be sealed with an even surface. In certain exemplary embodiments according to the present invention, the even surface which intersects the opening in its whole extent or which contains the complete rim is arranged perpendicular to an axis of rotation of the seal section around which it is turned from the first to the second position In some exemplary embodiments according to the present invention of the port, the secondary channel aperture and/or the septum aperture leads in each case completely or at least for example about halfway into a straight section of a cross-section of the lumen (or its boundary) of the main channel. The other half or the other part here lies in a round, rounded or curved section of the cross-section.

In certain exemplary embodiments according to the present invention of the port, the secondary channel aperture has neither an exclusively even nor an exclusively uniformly curved opening area.

In certain exemplary embodiments according to the present invention of the port, the septum aperture has an exclusively even opening area.

In some exemplary embodiments of the port according to the present invention, the seal section comprises a sealing surface on the face. This sealing surface is arranged to be moved from a first position to a second position along a turning radius and/or on a turning radius upon turning of the seal section. Thereby, the sealing surface closes, seals or covers the secondary channel aperture in the second position. In the first position, the sealing surface does not close, seal or cover the secondary channel aperture. The sealing surface thereby extends in parallel to a main cross-section plane of the seal section, i.e., perpendicular to its rotation or longitudinal axis.

In some exemplary embodiments according to the present invention of the port, the seal section comprises a sealing nose which in the axial direction of the seal section—or on the face—projects over the seal section. Thereby, the sealing nose is arranged for being moved on a turning radius from a first position into a second position on the turning radius upon turning of the housing element, or upon its transfer from one position into the other. The sealing nose in the second position thereby closes, seals or covers the secondary channel aperture, whereas in the first position, the sealing nose does not close, seal or cover the secondary channel aperture.

In certain exemplary embodiments according to the present invention of the port, the sealing nose in the second position closes, seals or covers the secondary channel aperture, e.g., with at least a partially ascending sealing surface—for example, relative to a main cross-section plane of the seal section.

In some exemplary embodiments according to the present invention of the port, the housing element comprises at least one section (also designated as "switch cup" herein). This section comprises a recess to intake the herein movable sealing nose. It further comprises or adjoins the secondary channel aperture.

In certain exemplary embodiments according to the present invention, this section has a basically circular cross-section.

In some exemplary embodiments according to the present invention of the port, the sealing nose comprises a groove which is open both to an end face of the sealing nose and to a lateral side surface of the seal section.

In some exemplary embodiments according to the present invention, the open groove is a secondary channel, or a section hereof, which is arranged in the seal section or in the seal element.

In certain exemplary embodiments according to the present invention of the port, the groove in the first position of the seal section fits against an opening of the secondary channel tube in such a way that it continues the flowpath of the secondary channel pipe over or across the seal section. Thereby, in the second position of the seal section the groove is not in fluid connection with the secondary channel tube or its opening.

In some exemplary embodiments according to the present invention of the port, the seal section comprises in addition to the sealing surface on the face or in addition to the sealing nose an elevated seal structure which is closed in its circumference and which in the second position of the seal section seals the opening of the secondary channel tube or prevents an escaping of fluid from the opening.

"Elevated" means in some exemplary embodiments according to the present invention that the seal structure is raised above a level of the side surface of the seal section.

In some exemplary embodiments according to the present invention, the closed seal structure is located at a side surface or circumference of the seal section.

In certain exemplary embodiments according to the present invention of the port, the seal section is designed as a separate seal element; in certain exemplary embodiments according to the present invention, it is designed in one piece.

In some exemplary embodiments according to the present invention, the seal element is produced from a different material than the housing element and/or the actuation element.

In some exemplary embodiments according to the present invention, the seal element in use is located between the housing element and the actuation element.

In some exemplary embodiments according to the present invention of the port, the seal section comprises at least one pierceable septum.

In certain exemplary embodiments according to the present invention of the port, both the septum aperture and the secondary channel aperture are arranged together in a cross-section half of the main channel.

The blood hose according to the present invention comprises in some exemplary embodiments according to the present invention at least one arterial patient line and at least one venous patient line.

In some exemplary embodiments according to the present invention of the blood hose, the port according to the present invention is inserted in the arterial patient line.

In some exemplary embodiments according to the present invention, the medical treatment apparatus is embodied as a blood treatment apparatus, in particular as an apparatus for apheresis or dialysis, again in particular for hemodialysis, hemofiltration, hemodiafiltration, peritoneal dialysis, acute dialysis etc.

Some or all of the exemplary embodiments according to the present invention can comprise one or more of the above or following advantages. Thereby, for a better understanding, exemplary embodiments are described with reference to the figures.

The port according to the present invention comprises at least one secondary channel which is connected to the main channel via a closable opening. The secondary channel can establish fluid connections to further sections of a fluid system. It can exemplarily lead to a secondary channel connector which advantageously is a detachable fluid connection to a fluid hose. Through this secondary channel, a further fluid can advantageously be added into the main channel or samples of the first fluid can be extracted from the main channel.

The mechanism which opens or closes the connection of the secondary channel to the main channel has at least one position in which the main channel is advantageously dead space free or substantially dead space free separated from the secondary channel.

The port or combiport according to the present invention can have at least the two valve positions: "closed" and "open". Additionally, the valve mechanism can advantageously serve to reduce extracted or fed fluids in a stepless and finely stepped way. Optionally, one of the two valve positions or a third valve position can advantageously be used to set an adjustable preloaded check valve with release function exclusively for inflows. Further, the valve position can advantageously be mechanically monitored.

In some exemplary embodiments according to the present invention, the port according to the present invention is embodied to be taken into or onto an intake. The intake may for example be provided at the front or a different section, in particular of the housing, of the treatment apparatus. The intake preferably serves to detachably fix the port. The port may be for example latched, snapped, clamped, mounted or attached, or the like. The user may thus see the valve position of the port together with or in synopsis with other devices or displays, so to speak at one glance and in the context with these.

In addition, it is possible and provided in some exemplary embodiments according to the present invention to have the existence of the port at the treatment apparatus (for example, in or at the intake) and/or its valve position read out automatically by the medical treatment apparatus. A corresponding device which is, e.g., equipped by means of an optical sensor, colour sensor, or the like, may be provided at the treatment apparatus. The thus obtained information can be further used in the control or regulation of the treatment apparatus.

The port according to the present invention in some exemplary embodiments according to the present invention advantageously consists of only three components. Thus, a compact packaging assembly is enabled.

Additionally, the port according to the present invention in some exemplary embodiments according to the present invention enables at least one hose or hose section used in conventional port solutions to be dispensed with. Thus, a buckling of this hose is prevented.

Because of the small overall length, the port advantageously requires little space during its use.

The access points known so far from the state of the art exhibit dead flow spaces between the lumen of the main channel and the sealing septum, or between the lumen of the main channel and the shut-off valve of the secondary channel. These dead spaces cause air pockets at system filling through the main channel. The first fluid flowing through the main channel, in most cases blood, further penetrates into these dead spaces. Blood, because of insufficient flow and because of the contact of the blood with air can quickly clot there. This is advantageously avoided by means of the port according to the present invention in some exemplary embodiments.

Given that such penetration in the (according to the present invention not present or at least minimized) dead spaces according to the present invention is avoided, with the first—but also with later—addition of a second fluid via the secondary channel aperture or via the septum into the main channel, such damaged or clotted blood is not returned into the main channel, which is a further advantage.

Also, it is advantageously prevented that an air hole infuses via the secondary channel aperture into the main channel at first use of the access point, as is known from constructions with a conventional piece of hose and hose clamp.

In balancing arrangements, the volume flows have to be as precisely as possible definable. Because of the compressibility of the air column in the dead flow spaces, falsifications in the volume flows and varying results in pressure measurements can be caused. This is not the case according to the present invention, as dead spaces are avoidable according to the present invention.

The port according to the present invention further does without a hose clamp to shut off the secondary channel. This is advantageous for several reasons. On one hand, according to the present invention the hose clamp is not necessary, which can save cost and effort. Moreover, it is frequently seen with hose clamps that they fatigue when closed for long periods of time as is the case with delivery of the fluid system with closed clamps. That also applies to the material of the hose section being clamped. In particular, on opening a hose clamp that had been closed for a long period, the hose regularly either does not open or opens only partially. As a rule, an impression remains at the clamping point which significantly increases the tendency to kink or buckle at this point. These disadvantages are advantageously avoided by means of the port according to the present invention without hose clamps.

In a closed position, fluid systems with hoses and hose clamps made from cost-effective thermoplastic materials are in general not suitable for being sterilized with steam, because both constituents become permanently damaged through the normal temperature of 121° C. The thus initially necessarily open (initial-) position of the hose clamps requires either a second closure, for example a tight Luer protective cap, or it requires that the user when setting up the treatment apparatus must under no circumstances forget to close the hose clamps before use of the port. This poses the risk that this is forgotten.

Generally for steam sterilization, Luer protective caps without a seal function are required. These contain one steam admittance point usually imperceptible or barely perceptible from outside. Since the predominant number of commercially available fluid systems are not steam-sterilized, it is difficult to explain to the user that he cannot depend on the sealing effect of the Luer protective caps, but that he has to close all clamps, which has to be done with other systems only before he removes the protective caps.

These uncertainties and risks no longer apply when using the port according to the present invention. The port according to the present invention can advantageously be sterilized and stored in all valve positions.

Because the port according to the present invention in certain exemplary embodiments according to the present invention comprises no dead spaces, its use in a fluid system does not exclude a reverse arterial blood return at the end of treatment. The dead space free arrangement, which is necessary for such a blood return as in such methods none of an air separation chamber, a clot trap or an air detector prevent air and damaged blood from entering the human body from the dead space area, is advantageously ensured by the port according to the present invention.

In a preferred exemplary embodiment, the housing element can be injection-moulded with the main channel and thus advantageously particularly cost-effectively from thermoplastics.

The present invention advantageously provides a repeatedly openable and closable port. It allows connection and disconnection also during the treatment of the patient without loss of liquid and undesired entry of liquids or air into the main flow.

A further advantage arising from this manufacturing process is that no gluing or welding has to take place. Further, the manufacture can readily take place exclusively automatically or mechanically.

In some exemplary embodiments according to the present invention of the port, it additionally comprises a self-closing or self-sealing pierceable septum. Through this, a fluid can be taken from or introduced into the main channel free of dead space by means of a cannula.

The seals of the port according to the present invention in some exemplary embodiments are advantageously bi-directionally self-reinforcing.

The use of polypropylene (PP), as provided in some exemplary embodiments, permits a cost-effective, environmentally neutral and biologically neutral manufacture of the port. PP is furthermore advantageously sterilizable with all known methods, that is, gas-, steam- and radiation-sterilizable.

The actuation of the port and in particular of the actuation element is advantageously equally possible for right- as well as left-handed users.

The present invention advantageously permits a good view of the valve position from distance.

Sensor monitoring of the current valve position by means of the treatment apparatus is advantageously optionally feasible with the present invention, likewise the possible active blocking of a valve position through the apparatus or mechanical actuation of the valve position. In this manner, a new level in treatment security and user guidance can be achieved.

By integrating the secondary channel aperture and the septum aperture in a single or in few components, the function security is advantageously increased and the manufacturing expense minimized.

Furthermore, the parts which rotate relative to one another, i.e., the housing element, actuation element and sealing element are advantageously permanently sealed against fluid escape and fluid ingress (gases and liquids) between the first fluid and the environment, and vice versa. This is achieved in certain exemplary embodiments according to the present invention by means of a permanently preloaded radial, semi-axial or axial seal arrangement. The seal section, or the seal element, consequently also takes on this stuffing-box seal function. Further seals, i.e., besides the respective one-piece rotating parts, are thus advantageously not required.

The present invention advantageously proposes a re-drying drainage for the septum aperture.

A re-drying drainage in some exemplary embodiments according to the present invention comprises—or consists of—one or more capillary structure(s) for conducting or guiding liquid away from or towards a functional element (e.g., the septum).

The present invention advantageously encompasses in some exemplary embodiments a double protection against inadvertent contact with the septum.

The cannula guide encompassed by the present invention advantageously comprises a protection against incorrect piercing of the septum.

The present invention thus advantageously offers protection from spreading particles across the septum into the first fluid.

The present invention advantageously comprises a simple, reliable snap-on retainer for apparatuses.

A view on the position pictograms which are switching position dependent on the switching position of the valve is advantageously encompassed by means of the present invention.

The present invention advantageously permits through its design a colour-coding of its actuation element, as it is not in contact with the first fluid.

Exemplary embodiments of the present invention are explained below in greater detail with reference to the accompanying drawings, in which identical reference numerals denote same or similar parts.

BRIEF DESCRIPTION OF THE DRAWINGS

FIG. 1a shows a port of a first exemplary embodiment according to the present invention in a slightly perspective view in the second position or the closed valve position.

FIG. 1b shows the port of FIG. 1a in the first position or the open valve position.

FIG. 1c shows a front view of a port of a second exemplary embodiment according to the present invention in the closed valve position.

FIG. 1d shows the port of FIG. 1c in the open valve position.

FIG. 1e shows a further exemplary embodiment of a port according to the present invention viewed from the front.

FIG. 1f shows an exploded view of the port according to the present invention of FIGS. 1a and 1b.

FIG. 3 shows the port of FIG. 2a in a slightly perspective view with the septum pierced through.

FIG. 5b shows a complete peripheral section through the port according to the present invention of FIG. 5a in the open valve position, slightly turned as compared to the illustration of FIG. 5a.

FIG. 15b shows the port according to the present invention of FIG. 15a in the open valve position.

DETAILED DESCRIPTION

Figure 2A:
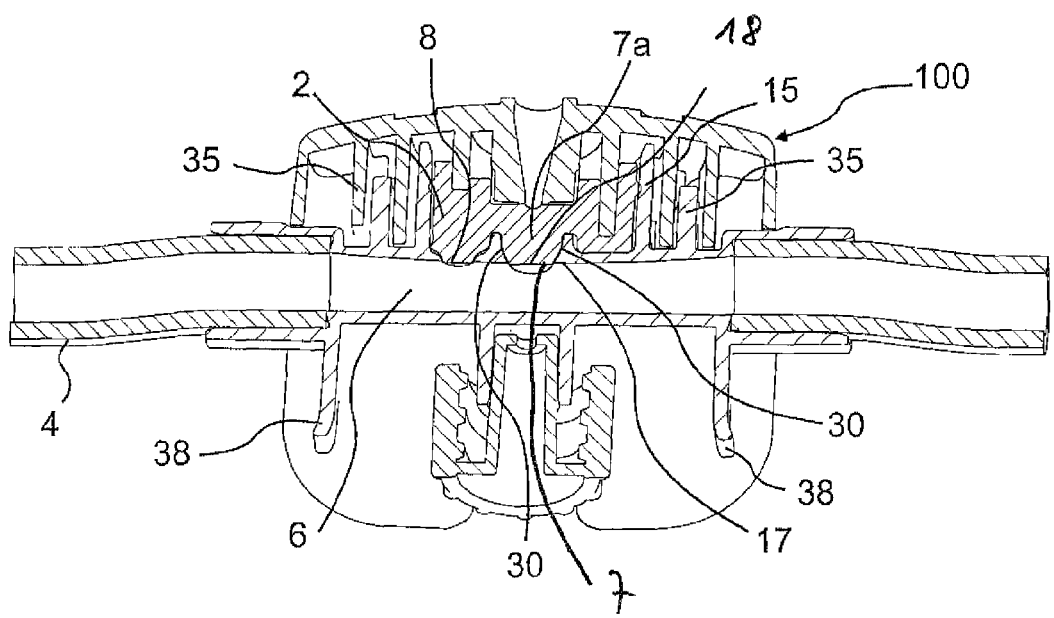
FIG. 2a shows the port according to the present invention of the first exemplary embodiment according to the present invention in longitudinal section in the closed valve position.

The port according to the present invention exemplarily described in the following comprises a main channel for a fluid and is intended using this to be integrated in a hose line. The port comprises in addition a septum access point and a secondary access point. The secondary access point is designed to be switchable; it is for example a Luer-port access point. The access through the secondary access point can be open (open or first position of the seal section, also denoted as open valve position) or closed (closed or second position of the seal section, also denoted as closed valve position). The seal section is, by means of an actuation element of the port, switchable between at least these two positions.

FIGS. 1a to 1f show two ports or combiports according to the present invention, in each case different from one another, here denoted as ports 100, partly in different valve positions, partly in different views.

FIG. 1a shows in perspective view a first exemplary embodiment of the port 100 according to the present invention, with a housing element 1 with a piercing protection plate 1a, an actuation element 3, a protective cap 5 seated on a secondary channel tube 11 and a main channel 6. The main channel 6 is connected to connecting hoses 4 by means of two hose sleeves 6a.

The housing element 1 in certain exemplary embodiments consists of or comprises an injection-moulded thermoplastic. The housing element 1 can be one-piece.

The seal section not shown in FIGS. 1a to 1e, also designated as valve, the port 100 according to the present invention is arranged due to the second position of the actuation element 3 shown in FIG. 1a in a closed, second position (closed position or closed valve position). The closed position is indicated by means of pictograms 39 which are intended as an optical indication of the valve position.

The protective cap 5 closes or seals an opening of a secondary channel connector of the secondary channel 11 not indicated by a reference numeral in FIG. 1a.

In FIG. 1b, the seal section, which is not illustrated here, and respectively the valve occupies the open or through-flow first position (open position or open valve position) due to the first position the actuation element 3 has taken. The open position is in turn tactilely and optically recognizable with the help of the sections of the pictograms 39 not covered by the actuation element 3. The pictograms 39 indicate by means of waveform that in each position of the actuation element 3 fluids or liquids can freely flow through the main channel 6. In this exemplary embodiment, the actuation element 3 in its first position obscures a stop symbol (X) and leaves only a flow symbol visible. It indicates that fluids or liquids can also flow through the secondary channel because of the open position of the seal section which it always occupies when the actuation element 3 is in the first position, or that a fluid connection between the secondary channel and main channel 6 exists.

In FIG. 1b the port 100 according to the present invention is shown with protective cap 5 removed. The secondary channel connector 12 in FIG. 1a covered by the protective cap 5 which is shown exemplarily as a Luer-port is now clear. In the open valve position, through for example a hose, a second fluid can be introduced through the secondary channel tube 11 into the port 100. The secondary channel connector 12 may serve to connect the hose with the port 100.

In addition to and/or independent of providing pictograms 39, however, the external design of the actuation element 3 and its respective rotational position in some exemplary embodiments according to the present invention also indicate the respective valve position. For example, in FIG. 1b other than that in FIG. 1a, a connecting line extends between knobs 3a and 3b of the actuation element 3 in the open valve position in the direction in which also the secondary channel tube 11 extends. Thus, the open valve position is intuitively already indicated from the position occupied by the actuation element 3 in FIG. 1b; at least, the valve position can be read at the position of the actuation element 3. By virtue of the design of the actuation element 3, the valve position can in addition be recognizable from a considerable distance.

FIGS. 1c and 1d show a second exemplary embodiment according to the present invention of the port 100 with a deviation against the first exemplary embodiment of the arrangement of the pictograms 39. These are provided in FIGS. 1c and 1d at or on the actuation element 3. Additionally, the imprint of four arrows which are provided likewise at or on the actuation element 3, indicate a septum piercing aperture centrally situated in the actuation element and an insertion channel 31. Both the housing element 1 and the actuation element 3 can thus already through the aforementioned pictograms 39 ease the operation of the port 100 and increase the security when operating it.

The valve of the port 100 according to the present invention in certain exemplary embodiments can be in a restrictive flow position, i.e., neither fully open nor fully closed and hence allow at least a slight flow from the main channel 6 into the secondary channel tube 11 (or vice versa). The size of the restriction can likewise be indicated by means of a corresponding design of the pictograms 39, perhaps in the form of an arrow with increasing thickness. FIG. 1e shows an example of one such designation. For example, in FIG. 1e an extra arrow 3c on the actuation element 3 points to a corresponding section of a crescendo symbol 39a and thus indicates the current restriction level for an exemplary embodiment of the port 100 with stepless intermediate positions.

Furthermore, distinct detent torque, which are described hereafter, between the end position of the actuation element 3 as well as rigid rotation stops provide the user with a reliable haptic feedback of the rotation process as well as of the valve position effected.

FIG. 1f shows an exploded view of the port 100 shown in FIGS. 1a and 1b. In addition to the elements shown in the preceding Figures, a sealing element 2—as an example of an exemplary embodiment of a separately present seal section—and a structure here designated as switch cup 15 of the housing element 1 can be recognized.

The switch cup 15 comprises a longitudinal axis which can at the same time be its axis of symmetry and/or rotational axis. The axis extends, in particular substantially or completely, vertically to diagonally to the longitudinal axis of the main channel 6 further explained below, which in turn can be its axis of symmetry. The switch cup 15 is, preferably completely or substantially, formed as a cylinder or has cylindrical sections. It can be a guidance- and/or seal-partner for the sealing element 2 and/or for the actuation element 3. Because of its geometry, the switch cup 15 permits rotational movement of the seal element 2 with which it is connected and/or the actuation element 3 with which it is connected.

The seal element 2 consists in certain exemplary embodiments of an injected or pressed elastomer. Elastomers advantageously distinguish themselves through particularly low creep behaviour under load. Thereby, a constant sealing effect during the operating time of the port 100 and also after extended storage of the port 100 can be guaranteed.

In some exemplary embodiments according to the present invention, in which exclusively a secondary channel is switched or restricted, an injection-moldable silicon rubber material is advantageously used as this is particularly precise in manufacture and low in creep.

In some exemplary embodiments according to the present invention, in which the seal section or the seal element 2 is moreover to allow access to the main channel 6 through the septum 7a (see FIG. 2a), preferably elastomeric compounds based on isoprene rubber are used. These elastomers are particularly suitable to sealing again after the removal of a cannula from the septum 7a.

For exemplary embodiments with low requirements for creep resistance, seal pressure or reclosure, in particular for applications in which no steam sterilization treatments are needed, thermoplastic elastomers can preferably also be used. These are characterized by lower material costs and by producibility by cost-effective thermoplastic injection-moulding process.

After-treatments at the finished seal element 2 in the form of post-tempering or post-curing, washing or by coating with silicon oils can advantageously be carried out with all the mentioned materials. In this way, the creep resistance and the absence of particles can be increased and the static friction and sealing effect in comparison with other elements improved.

The actuation elements 3 in some exemplary embodiments according to the present invention are likewise made from or comprise an injection-moulded thermoplastic.

In some exemplary embodiments according to the present invention, as that shown in FIG. 1a for example, a multitude of functions is integrated in the actuation element 3. These exemplary embodiments include the well grippable, ergonomically rotatable knobs, impressed pictograms, locking catches for permanent latching with the housing element, rotation stops, rotation detents, lugs for sensor monitoring and more.

The actuation element 3 of FIGS. 1a to 1f can advantageously be cost-effectively and reproducibly manufactured in simple open/closed injection moulding tools.

As no part of the surface of the actuation element 3 is in contact with the liquids to be treated such as blood, the actuation element 3 can advantageously be coloured. Special, compatible pigments are advantageously not required.

Additionally shown in FIG. 1f is an intake to temporarily intake or fix the protective cap 5 at the port 100. In or on this, the protective cap 5 can be stored as long as it is not needed. Such an intake for the protective cap 5 can naturally also be suitable for intaking the protective caps of other medical apparatuses. The protective cap held therein does not have to be that with which the secondary tube connector 12 is covered. It does not even have to be a part of the port 100 according to the present invention.

In the exemplary embodiments of FIGS. 1a to 1f, only the three components, housing element 1, seal element 2, and the actuation element 3, are essential. The additionally shown elements such as the protective cap 5 are purely optional.

Furthermore in other exemplary embodiments than those shown in FIG. 1a to 1f, the seal element 2 is not required. So, for example, in the case that the seal element 2 is manufactured from or with thermoplastic elastomers, the seal element 2 can be manufactured integral with optionally the housing element 1 or the actuation element 3—for example through welding (after pigmentation of a joining part for example also by laser absorption welding) or through two-component injection-moulding, through other means or in one-piece. This firmly bonded connection can offer advantages, such as for example, the precision of the alignment of the one or the other position of the seal section (here also denoted as switching angle) can be increased, material can be saved as the inherent rigidity of the seal element can be lower, or manufacturing time can be saved as sorting and handling procedures are dispensed with.

The main channel 6 shown only in outlines in FIGS. 1a to 1f is embodied as a tube which is closed in its circumference. The tube comprises coaxial female hose sleeves 6a which are arranged on the ends. The main channel 6 is by means of its hose sleeves 6a on both sides via connecting hoses 4 glued in or welded on the hose sleeves 6a connected to a fluid system, for example a blood hose according to the present invention. The housing element 1 forms the major part or the whole part of the fluid-conducting structures of the main channel 6, of the secondary channel not recognizable in FIGS. 1a to 1f and of the access to the likewise not illustrated septum.

If the housing element 1 is integrated in for example one-piece cassette single use fluid systems, it can advantageously be possible to form the main channel 6 and/or the secondary channel not as a closed tube, but rather in a split or half-open form. In this manner, other connections of the fluid paths of the port 100 to the other fluid structures of the fluid system are possible. For example, main channels with flow axes that are not linear can be provided. The closure of the half-open channel structures can be carried out for example by means of additional injection-moulded elements or by means of pressed on, glued on, or welded on foils.

The main channel 6 is preferably designed as the shortest possible tube. As can be deduced from FIGS. 2a and 2b, there are two openings, apertures or bores (in the following for the sake of simplicity always designated as apertures or bores, irrespective of their manufacture) arranged in the wall of the main channel 6, the septum bore or aperture 7 and the secondary channel bore or aperture 8.

In some exemplary embodiments according to the present invention, in order to save space these two bores or apertures are arranged as closely as possible adjacent to one another.

Figure 3:
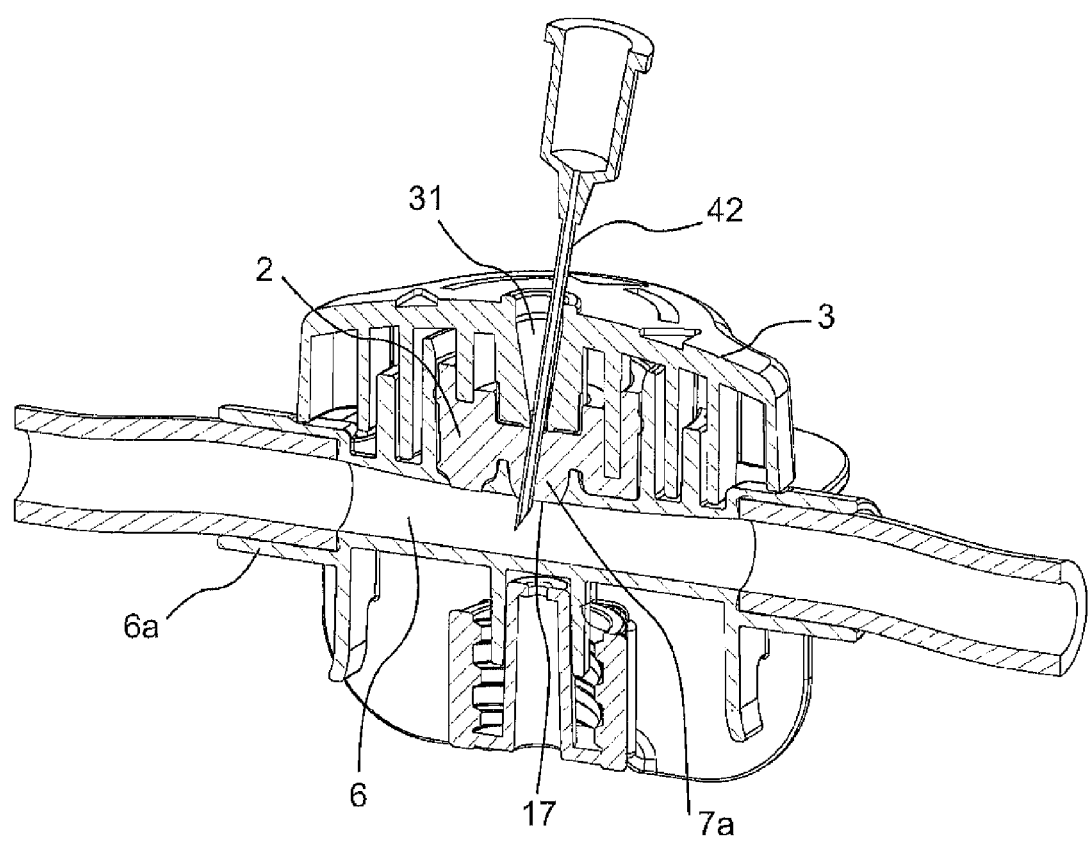

The septum bore 7 is closed or sealed by means of septum 7a. An access to the main channel 6 is possible by means of piercing the septum 7a, for example with the aid of a cannula 42 guided through the insertion channel 31, as is shown in FIG. 3. The secondary channel bore 8 connects the main channel 6 with additional fluid systems, as described below. The secondary channel bore 8 opens into the secondary channel not indicated by reference numeral which comprises or consists of secondary channels 9 and 10. The secondary channel continues in the secondary channel tube 11 and ends with regard to the port 100 in the secondary channel connector 12.

Both the septum bore 7 and the secondary channel bore 8 in the lumen or their opening area are formed as small as technically possible with regard to the flow. Thus, they advantageously exhibit in the closed valve position (for example, due to tolerances of the seal element 2) as well as in the open valve position the smallest possible impairment of flow in the main channel 6.

Independently of this, in some exemplary embodiments according to the present invention, the septum bore 7 and/or the secondary channel bore 8 of the port 100 according to the present invention are arranged substantially along a line parallel to the main flow axis, or together in one half of a cross-section, or in a main channel wall or shell of the longitudinally cut main channel 6. Thus, it is advantageously possible in exemplary embodiments other than those shown here, to design the main channel 6 as a half-open channel with solid channel walls. Its other half can, for manufacturing or for arrangement reasons, be embodied by a further housing element, likewise not shown here. The further housing element in such exemplary embodiments can be made from or comprise a different material than the rest of the housing element, for example a film. If both the septum bore 7 as well as the secondary channel bore 8, as in the exemplary embodiments according to the present invention shown here, open to or are located together on a main channel half-side (in longitudinal section) or together on a cross-section half, they thus advantageously allow to combine a multitude of seal functions in the seal element 2.

Deviating from this, it is however according to the present invention also considered to arrange the septum bore 7 and the secondary channel bore 8 opposite one another—in relation to the main channel 6 or the main flow axis. By one such arrangement the septum 7a can advantageously be arranged for good accessibility for the operator while the secondary channel bore 8 is arranged in the port 100 with respect to other considerations.

The main channel 6 is essentially of a cylindrical or prismatic base form of the cross-section. In some exemplary embodiments according to the present invention, the main channel advantageously comprises at least in the area of the septum bore 7 a flattened inner form 17, a straight cross-section section or a flat septum bore 7 (see FIGS. 2a and 2b). Thus, the seal element 2 can seal the septum bore 7 against the main channel 6 in a dead space free and positive or interlocking manner with a flat seal face, even if by turning the actuation element 3 the seal element 2 is transferred to a different position than the closed position or valve position.

Hereby, the design of the exemplary embodiments according to the present invention here presented of the main channel 6 differs for example from other exemplary embodiments which are likewise according to the present invention, in which the main channel 6 is exclusively cylindrical, at least always curved in the corresponding cross-section. With such an exclusively cylindrical—or in another mode curved—exemplary embodiment, the correspondingly designed septum 7a would, because of its cylindrical endface curve, no longer seal flush with the wall of the main channel 6, which also in the area of septum bore 7 is cylindrical, after turning the actuation element 3. These disadvantages are advantageously avoided through a flat design of a section of the main channel 6, here the flattened inner form 17.

In some exemplary embodiments according to the present invention, the septum bore 7 diameter is less than half the diameter of the main channel 6. With one such exemplary embodiment, an always sufficient sealing of the septum bore 7 through the septum 7a can be guaranteed also with a main channel 6 designed to be purely cylindrical—or otherwise curved. For this, the closing end face 18 of the sealing element on the main channel side can exemplarily comprise a rotationally symmetrical, dished-end like curvature. In one such exemplary embodiment or a similar exemplary embodiment, by turning the seal element 2, only very slight geometric bumps at the sealing of the main channel 6 against the septum bore 7 occur. Such deficiencies in the geometric correlation range in such cases in the area of less than 5% of the diameter of the main channel 6. Herewith, yet nearly flush and dead space free endings of the septum bore 7 in the periphery of the main channel 6 can be achieved. Hence, complex or elaborate injection moulding technology embodiments of the main channel 6 can advantageously be eliminated.

Figure 2B:
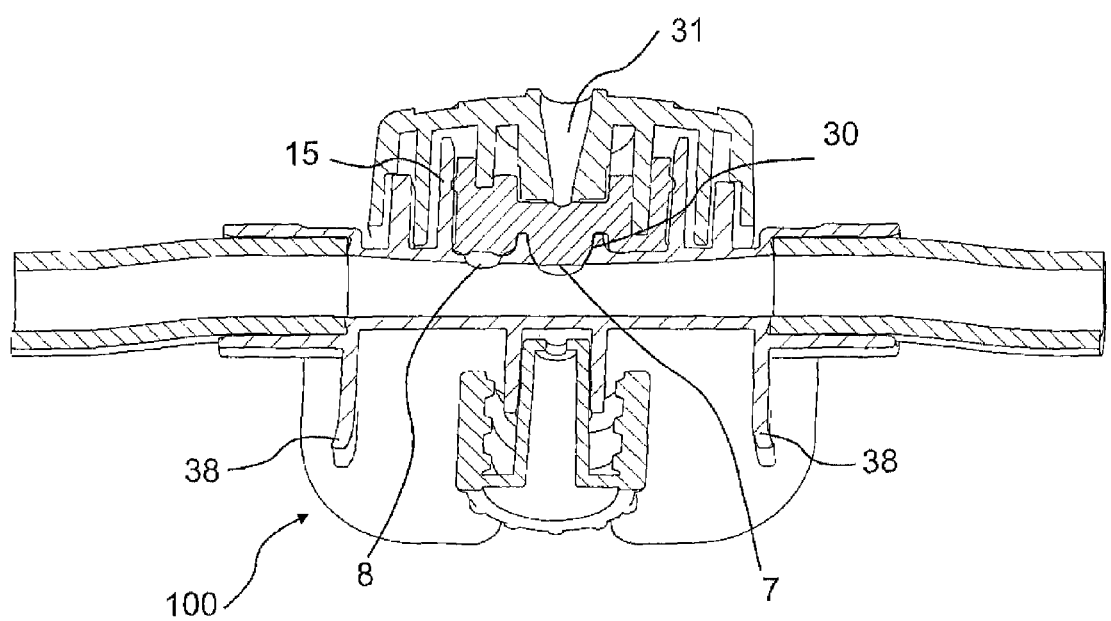
FIG. 2b shows the port of FIG. 2a in the open valve position.

The housing element 1 of the port 100 shown in FIGS. 2a and 2b comprises, on the side of the main channel 6 opposite the actuation element 3, fixing elements to fix or hold the port 100. Two or more walls or structures comprising snap-in tongues 38 and/or flexible ribs—as examples for fixing elements—enable the intake of the port 100, for example, into sockets or other fasteners of a treatment apparatus. Thus, since in the exemplary embodiment according to the present invention shown here, suitable, for example flexible and/or undercut, fixing elements are already included on the port 100, such elements which readily wear and become contaminated do advantageously not have to be provided in the treatment apparatus, for example in the socket.

In the socket of the treatment apparatus or in other fixing locations for the port 100, undercuts can advantageously be omitted even if on the port 100 insertion devices or suchlike are provided, which after insertion in a counterpart of the socket of the treatment machine achieve a suitably high retaining effect because of the friction to be overcome.

FIGS. 2a and 2b further exhibit sections of the switch cup 15 as well as bow ribs 35, each of which are described in detail herein, in each case in section.

In FIG. 3, it is shown how, by means of a cannula 42 which is guided through the insertion channel 31, the septum 7a is pierced through. Therewith, a fluid connection between cannula 42 and the main channel 6 is established.

Furthermore, the septum 7a (pierced or not) always ensures sealing of the septum bore 7 against fluid escape from the main channel 6, also with respect to the cannula 42. The choice of a corresponding material for the septum 7a supports this property benefit. Preferably, isoprene-, chlorobutyl- and bromobutyl-rubber compounds are used. This property is further benefited by a suitable thickness or wall thickness of the septum 7a and through the provision of a permanent pressure preload of the septum 7a. In the exemplary embodiment according to the present invention described here, the pressure preload is ensured through the specified flexible and shear elastic loading geometries between housing element 1 and actuation element 3.

The suitable thickness or wall thickness of the septum 7a is in some exemplary embodiments greater than twice the length of the oval shaped cannula lumen, which comes about through ensiform or sword-shaped bevelling, or greater than twice the diameter of the circular cannula cross-section.

Figure 4:
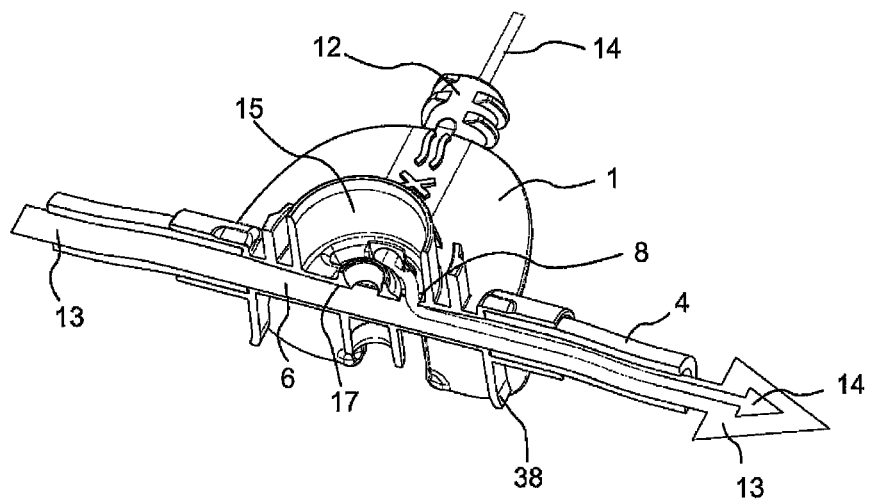
FIG. 4 shows the major fluid paths inside the port of FIG. 1a in a longitudinal section.

FIG. 4 shows the major fluid paths in the port 100 in a longitudinal section of the port 100.

A main channel flow 13 (large arrow) flows through the main channel 6 from left to right and consequently establishes a fluid connection between the two connecting hoses 4.

A secondary channel flow 14 (small arrow) flows through the secondary channel connector 12 into the secondary channel tube 11 and onward through the secondary channel bore 8 into the main channel 6. The secondary channel flow 13 together with the main channel flow 14 leaves the port 100 through the connecting hose 4 situated on the right in FIG. 4.

Figure 5A:
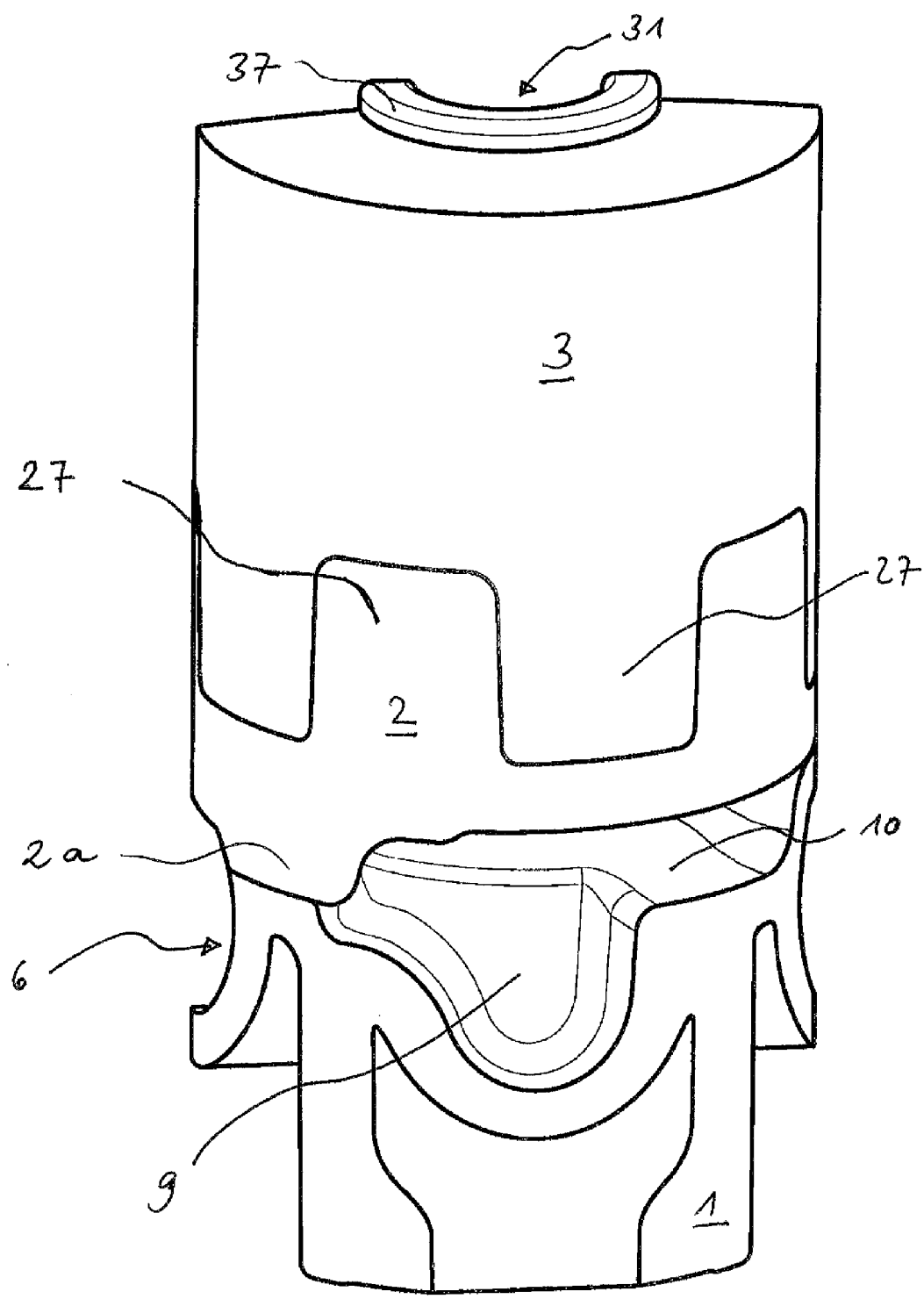
FIG. 5a shows a partial peripheral section through the port according to the present invention in the closed valve position.
Figure 56:
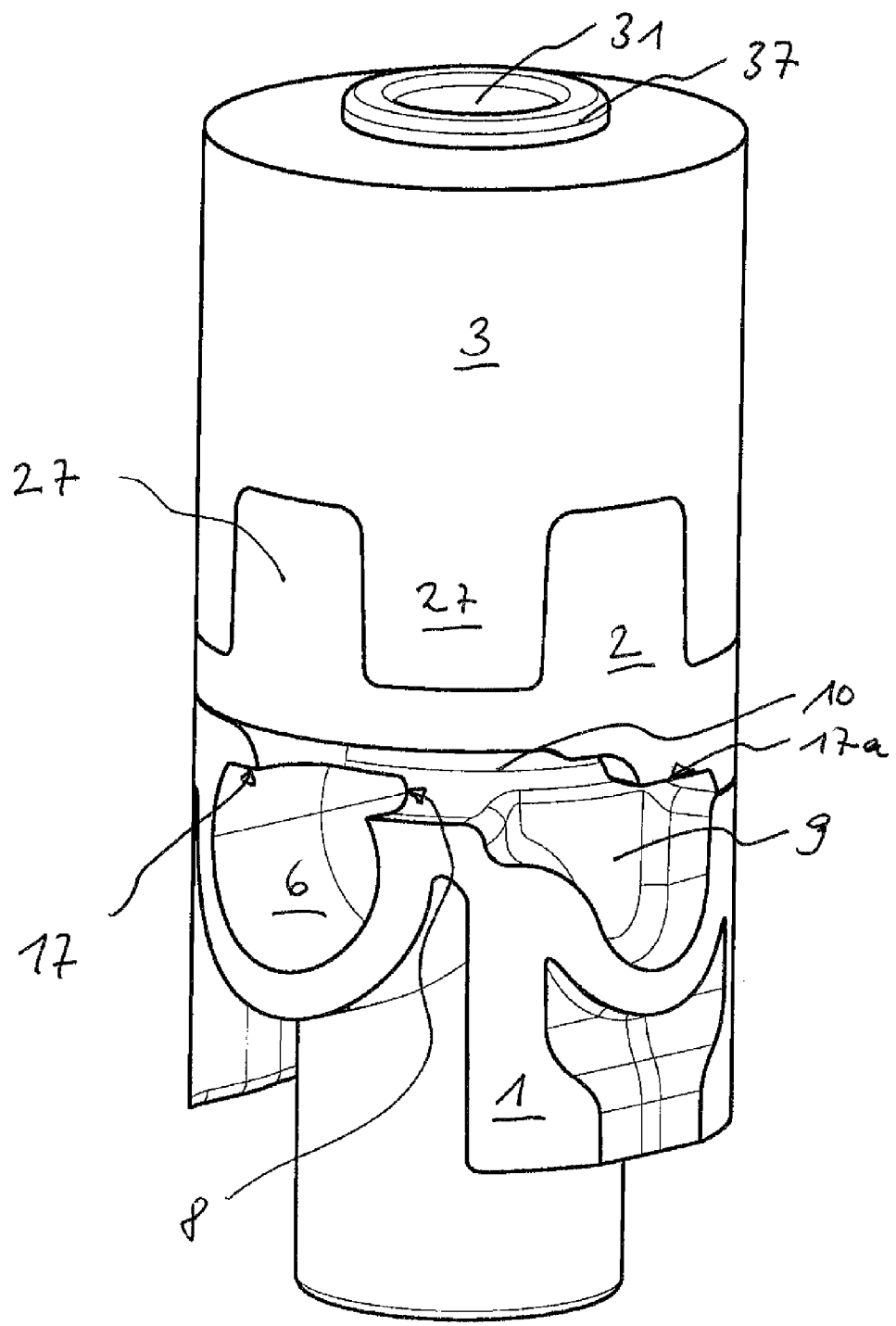

FIGS. 5a and 5b show sections of the port 100, in particular of the actuation element 3, with rotation carriers 27 which are designed as forks and pockets, in a peripheral section similar to a cylinder punched out of the port 100.

Thereby, FIG. 5a represents the closed (valve) position, FIG. 5b the open (valve) position. The representation of FIG. 5b is slightly turned compared to that of FIG. 5a.

It can be recognized in both Figures that the secondary channel which starts at the secondary channel bore 8 and which connects the main channel 6 in the open valve position through a secondary channel tube 11 and the secondary channel connector 12 to additional fluid systems as described below, partially runs—as secondary channel 9—in the housing element 1 whilst running to another part—as secondary channel 10—in the seal element 2.

Furthermore, in FIG. 5a, a section 2a of the seal element 2 can be recognized which in the closed valve position of this Figure effects a sealing of the secondary channel (reference numerals 9 and 10) against the main channel 6 by not leaving a gap between seal element 2 and the secondary channel bore 8 not shown in FIG. 5a. In FIG. 5b, this gap between the secondary channel bore 8 and seal element 2 exists, which is why the valve is open. A fluid which flows from the right hand edge of FIG. 5b for example in the secondary channel 9 of the housing element 1 can now flow under the seal element 2 through the exposed secondary channel opening 8 and through this in the main channel 6.

In FIG. 5b, it can be recognized that the main channel 6 in the upper area comprises a flattening or a flattened inner form 17 (in the sense of a straight section of the lumen of the main channel 6). In fact, the secondary channel opening 8 visibly opens partially into the flattened inner form 17, to another part in an area of the main channel 6 in which this comprises a circular cross-section. The seal element 2 can also in a section thereof comprise a flattening 17a. The flattening 17a can with the closed secondary channel bore 8 steplessly close or seal the upper area of the main channel 6 in which this is flattened.

Further to be seen in FIGS. 5a and 5b is a contact protection bar 37 which protects the opening area of the insertion channel 31. Both structures are explained herein with reference to FIG. 11b.

Figure 6A:
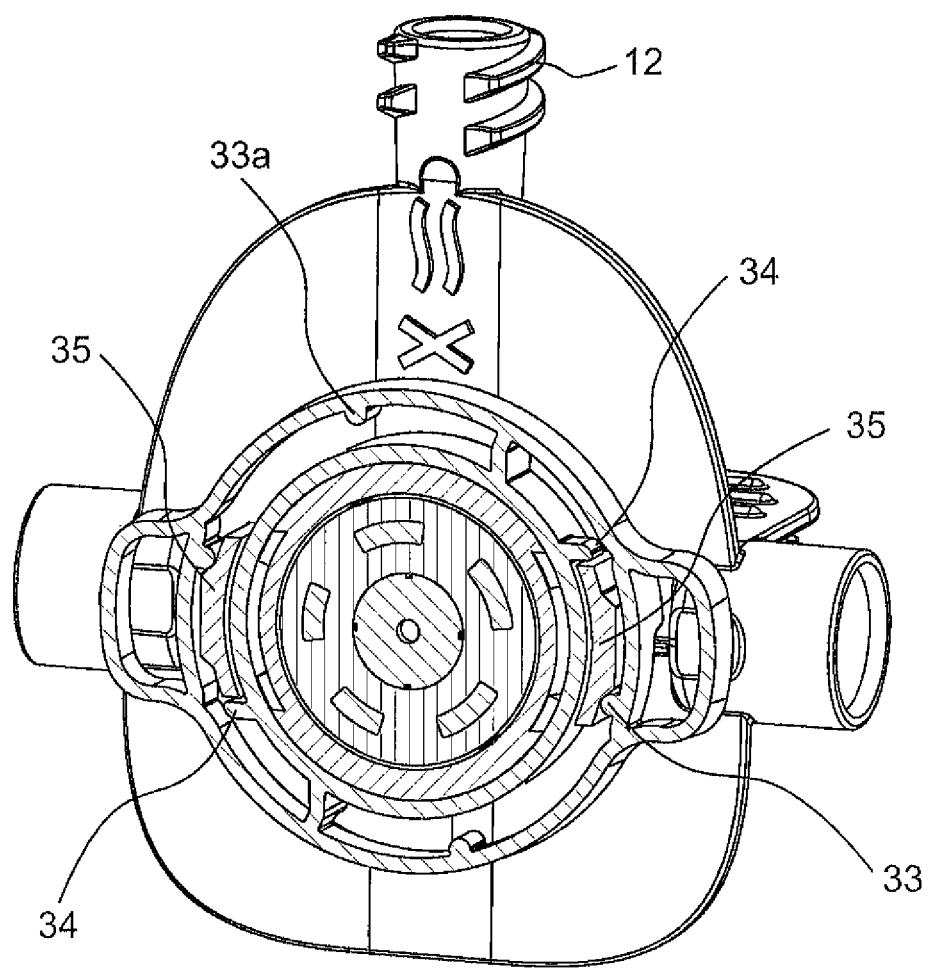
FIG. 6a shows the port of FIG. 1a with a frontal section of the actuation element.
Figure 6B:
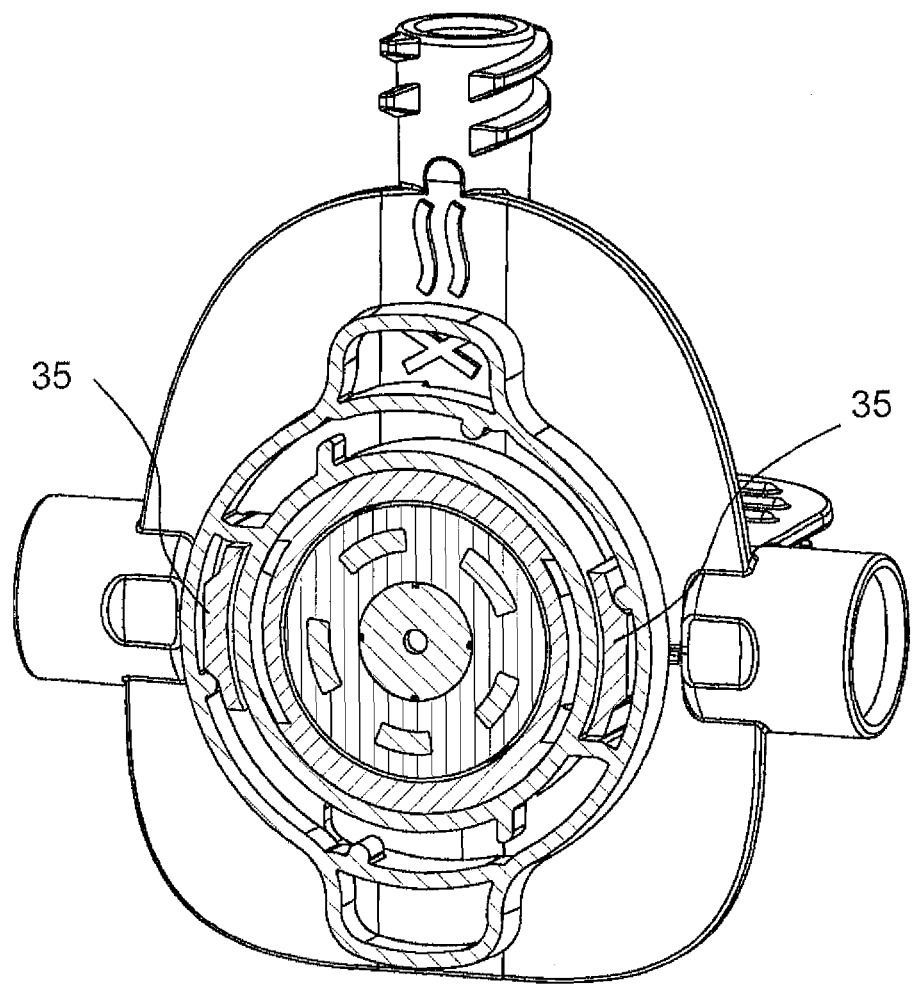
FIG. 6b shows the port of FIG. 6a in the open valve position.

FIGS. 6a and 6b show the port 100 in a frontal section of only the actuation element 3, in closed valve position (FIG. 6a) as well as in the open valve position (FIG. 6b). The actuation element 3 is sitting in FIG. 6a in its second position, in FIG. 6b in its first position. Both Figures show that the rotatable actuation element 3 comprises locking catches 33a for a rotation detent 33. They show additionally, that the housing element 1 comprises in two fixed bow ribs 35 locking recesses 33b to intake the locking catches 33a. By latching a first locking catch 33a in a first locking recess 33b, a first position of the actuation element 3 is fixed until actuated or turned again. By latching the first locking catch 33a in a second locking recess 33b (or a second locking catch 33a in the first locking recess 33b), a second position of the actuation element 3 is fixed for the time being. Thereby, it is immaterial whether the actuation element 3 comprises the locking catches 33a or carries the locking recesses 33b.

Through rotation stops or rotational movement stops 34—which are to be seen in FIGS. 6a and 6b—or other formed dead stops, the limits of rotation of the actuation element 3 can be fixed. Suchlike rotation stops 34 can be limited in their movement by means of the bow ribs 35, for example by edges or other sections of the bow ribs 35, as is seen in FIGS. 6a and 6b.

Both the rotation detent 33 and the rotation stops 34 can give the operator a tactile feedback of the valve position.

As both the rotation detent 33 and the rotation stops 34 are preferably external or at least arranged externally to the above mentioned fluid paths, they do not come into contact with any fluid. In or due to the absence of contact with fluid, no contamination of the fluids takes place even with material friction from the rotation detent 33 and the rotation stops 34. The rotation detent 33 and the rotation stops 34 due to the absence of contact with the fluid also cannot increase the fluid dead spaces. Moreover, on the same grounds they do not impair the air bleeding characteristics of the port 100.

In certain exemplary embodiments of the present invention, material contacts occur inside the switch cup 15 and in the area of the bow ribs 35 exclusively between the housing element 1 and the seal element 2. These can each be sealing and friction optimized in the contact and seal pressure zones. In such exemplary embodiments, in the fluid area there thus exist no abrading or grinding contact surfaces between the housing element 1 and the actuation element 3. The external surfaces of the switch cup 15 and the corresponding associated inner surfaces of the actuation element 3 in contrast undertake tasks for the play-free preloaded axial and radial guidance of the actuation element 3 against the housing element 1. Here, friction and also a certain abrasion can and may arise. Through the play-free design, the seal element 2 is guided centrally and with optimum preload to the housing element 1. Tipping and applications of force are absorbed by the actuation element 3 and thus not transferred to the seal element 2.

The bow ribs 35 which can be arranged radially further out, in pairs opposite each other, are productionally and functionally optimized in their design. As mentioned above, the bow ribs 35 of FIGS. 6a and 6b form with their side surfaces limits for the rotation stops 34 of the correspondingly arranged radial ribs of the actuation element 3. Through the curved development of the bow ribs 35, high stiffness and rigidity result, whereby the bow ribs 35 are at the same time angularly precise and protected against overloading. Through the curved form in conjunction with the thin wall thickness, a relatively thin rib is produced which causes, optimized using injection moulding technology, few shrink marks or sunk points in the main channel 6 lying beneath.

On the two bow ribs 35, the above mentioned locking recesses 33b are to be found, which intake the associated locking catches 33a of the actuation element 3 through elastic distortion of both the bow ribs 35 and the connecting bridges of the locking catches 33a by latching. The locking catches 33a and the locking recesses 33b are dimensioned so that preferably a play-free preload in the desired limit positions of the actuation element 3 is achieved. The triggering latching torques are so chosen that the operator receives a definite tactile feedback of the safe operation and furthermore the desired valve position is maintained with sufficient precision and lock. The overload resistance and the switching precision are more favourable, the further out radially the corresponding structures are arranged. Also for reasons of the overload resistance and the switching precision, the rotation stops 34 and the locking catches 33a or respectively the locking recesses 33b are provided point symmetric or mirror symmetric to one another in pairs. The force is thus halved while the stiffness is doubled. Furthermore the forces as a force couple are compensated to a pure torque, whereby tipping and bending moments between housing element 1 and actuation element 3 are avoided. For exemplary embodiments with desired rotational intermediate positions, the bow ribs 35 may optionally comprise roughened, fine toothed, or radially preloaded areas. Also hereby the operator can be advised by means of a fine detent or higher torque, in which rotation angle ranges a freely selectable and self retaining intermediate position can be adjusted.

On the other hand, the rotation angle ranges between the latching positions can also be intentionally configured for low friction. Thus after overcoming a locking recess 33b, an accelerated rotation of the actuation element 3 takes place until the next locking recess 33b is reached. Thus, the operator is again tactilely informed of the valve position.

In further exemplary embodiments according to the present invention, the rotation angle between two function positions is chosen intentionally so narrow that two adjoining locking recesses 33b merge into one another, thus exhibiting an approximate waveform. Thus, it can be avoided that by turning the actuation element 3, undesired intermediate positions can be taken up.

Figure 7A:
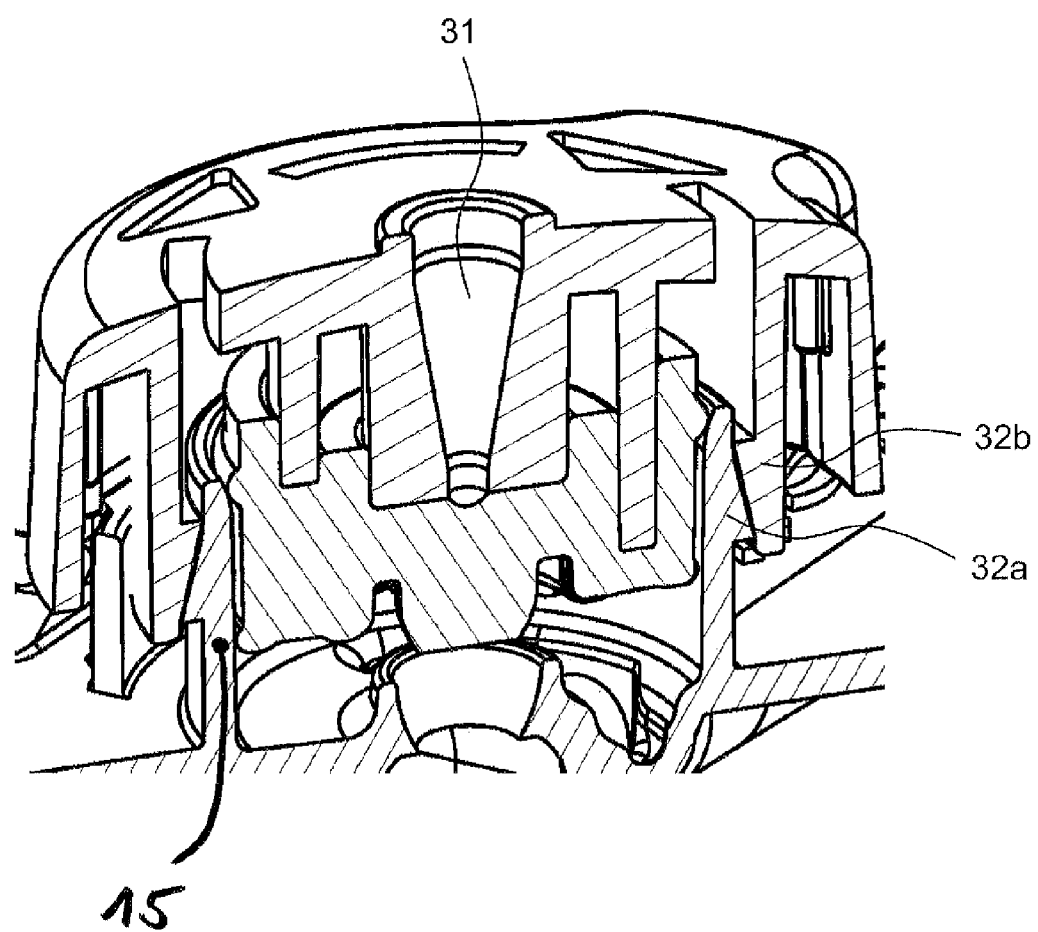
FIG. 7a shows the port according to the present invention in partial section directly before the actuation element is locked with the housing element.
Figure 7B:
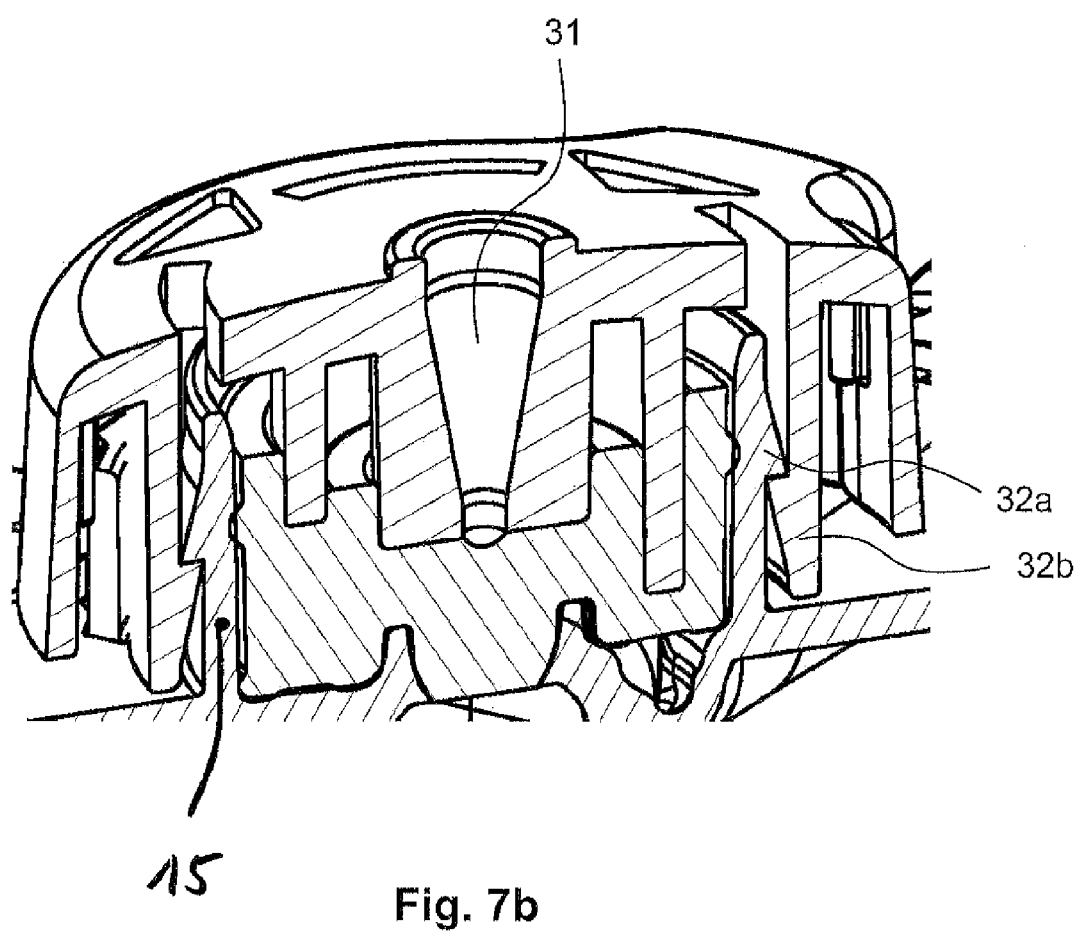
FIG. 7b shows the port of FIG. 7a in a locked condition.

As shown in FIGS. 7a and 7b, the switch cup 15 comprises in some exemplary embodiments of the present invention—in an arbitrary area, preferably however, as shown here, in an external position thereof—one or more locking catches 32a. In some exemplary embodiments according to the present invention, these are arranged radially a small distance from the centre of the switch cup 15.

The latching elements 32a of the housing element 1 can be latched to the locking recesses 32b of the actuation element 3. The latching created here holds the actuation element 3 to the switch cup 15 and by that to the housing element 1. For the person skilled in the art, it can be seen that the latching elements 32a can also be arranged in other places on the housing element 1 than the switch cup 15.

FIG. 7a shows the port 100 in a condition in which the actuation element 3 is not (yet) latched with the housing element 1. FIG. 7b shows the port 100 of FIG. 7a in a latched condition.

The latching elements 32a and 32b are in some exemplary embodiments according to the present invention designed for non-detachable and play-free connection between housing element 1 and actuation element 3, as in section arrow-shaped, complementary and radially completely or sectionally circumferential, that is to say in cross-sectionally closed structures.

The latching elements 32a and 32b are in some exemplary embodiments of the present invention formed similar to grooved serrations of hose nozzles.

The latching elements 32a and 32b serve to join together housing element 1 and actuation element 3. They can also be formed as snap elements.

In some exemplary embodiments according to the present invention, as in the one shown in the Figures, the latching elements 32a and 32b permit a rotational movement between the housing element 1 and the actuation element 3.

Because of their ramp-formed surfaces (in cross-section), only low assembly forces in the assembly direction are required to latch the latching elements 32a and 32b. In certain exemplary embodiments according to the present invention, in the disassembly direction however they prevent, by the faces arranged primarily vertical to the latching direction, any damage-free unlatching. In comparison to free-standing snap-in tongues, the cylindrically circumferential snap-in structures are with little material input considerably stiffer and firmer. Thereby, even with cost-effective unreinforced thermoplastics and also with wall thicknesses in the tenths of millimeter, favourable assembly forces in the region of 50N, which are coupled with advantageously high disassembly or destruction forces in the region of 500N, are realized.

Figure 8:
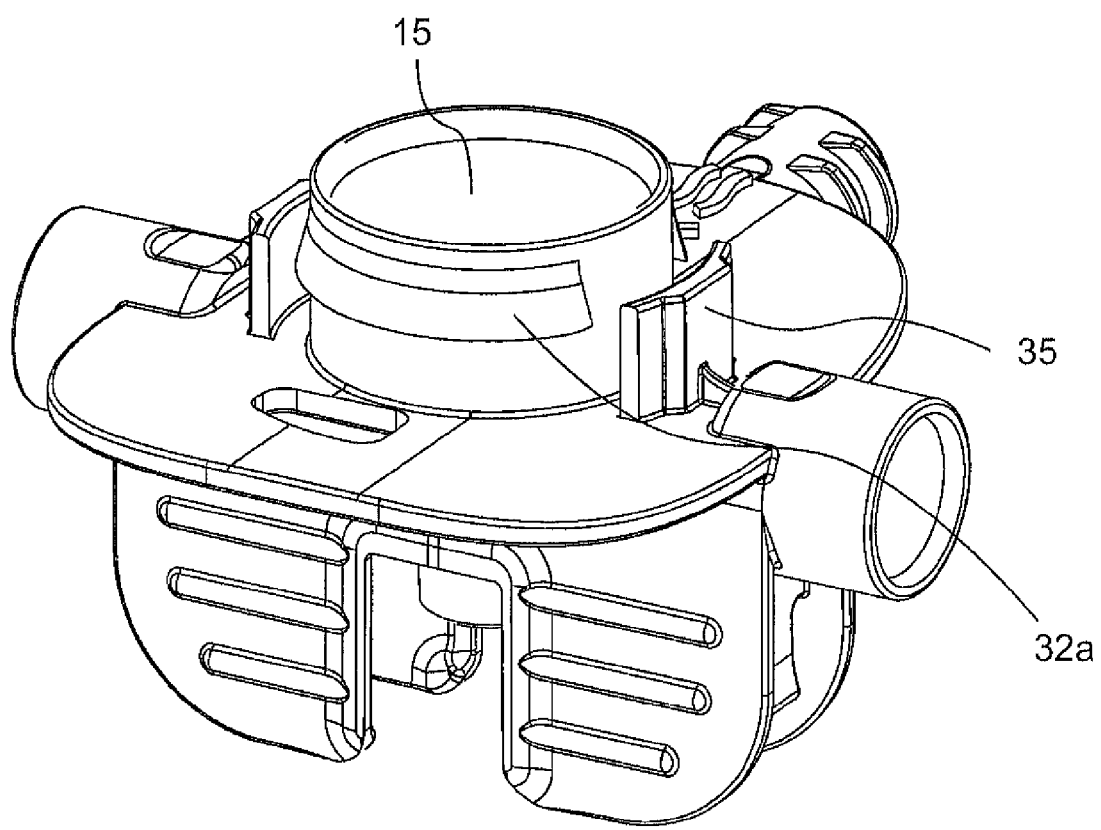
FIG. 8 shows the housing element of the port of the first exemplary embodiment in perspective view.

FIG. 8 shows the housing element 1 of the first exemplary embodiment of FIGS. 1a and 1b in perspective view. The switch cup 15 is shown, as are the bow ribs 35 arranged on both sides of the switch cup 15. These serve as a limit of a rotary movement of the rotation stops 34 as previously explained.

In the exemplary embodiment shown here of both the housing element 1 and also the actuation element 3, they can be manufactured by using particularly economical demoulding methods by means of injection-moulding. To produce the housing element 1, a standard combination of jaws and cores suffices as a tool, while for the actuation element 3 a so-called open-shut-tool is sufficient. By these demoulding methods, both the housing element 1 and also the actuation element 3 each can comprise one, two or more discontinuities in the otherwise circumferential latching or snap-in structure. The angular positions and the angular ranges of the remaining latching structures of both elements are in these cases so determined that in the preferred position of the actuation element 3 it comes to a maximum, but at least sufficient, overlap of the two latching elements 32a and 32b. But also in all other possible switch positions, a sufficient overlap is always provided for. In certain exemplary embodiments of the present invention, all or some of the latching elements 32a on the one hand and/or the latching elements 32b on the other hand are arranged in pairs opposite each other (for example mirrored or axisymmetrically with reference to a rotation center of the actuation element 3). Thus with a pre-existing axial preload effect acting on the latching, no undesired tilting of individual elements resulting herefrom arises.

Figure 9:
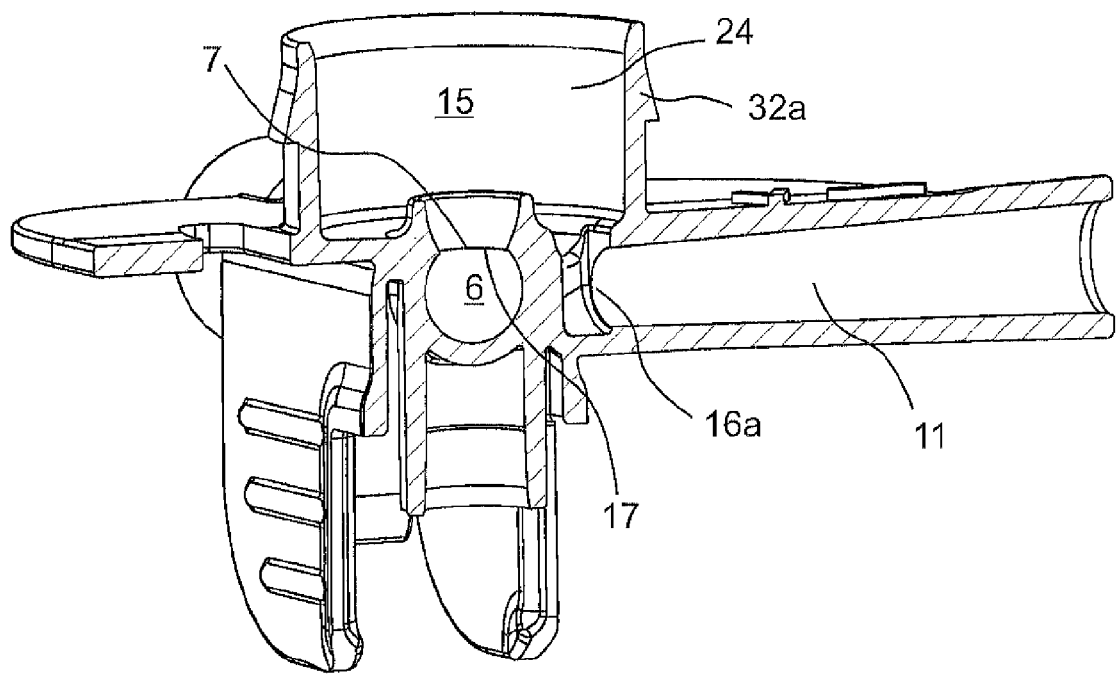
FIG. 9 shows the housing element of the port of the first exemplary embodiment in slightly perspective view in a longitudinal section through the secondary channel tube of the secondary channel.

FIG. 9 shows the housing element 1 of the port 100 of FIGS. 1a and 1b in a slight perspective in a longitudinal section of the secondary channel tube 11 of the secondary channel. A stuffing box packing zone 24 of the switch cup 15 is shown (see also FIG. 10).

The secondary channel tube 11 is in fluid connection with the main channel 6 via a secondary channel bore 16a of the switch cup 15.

Figure 10:
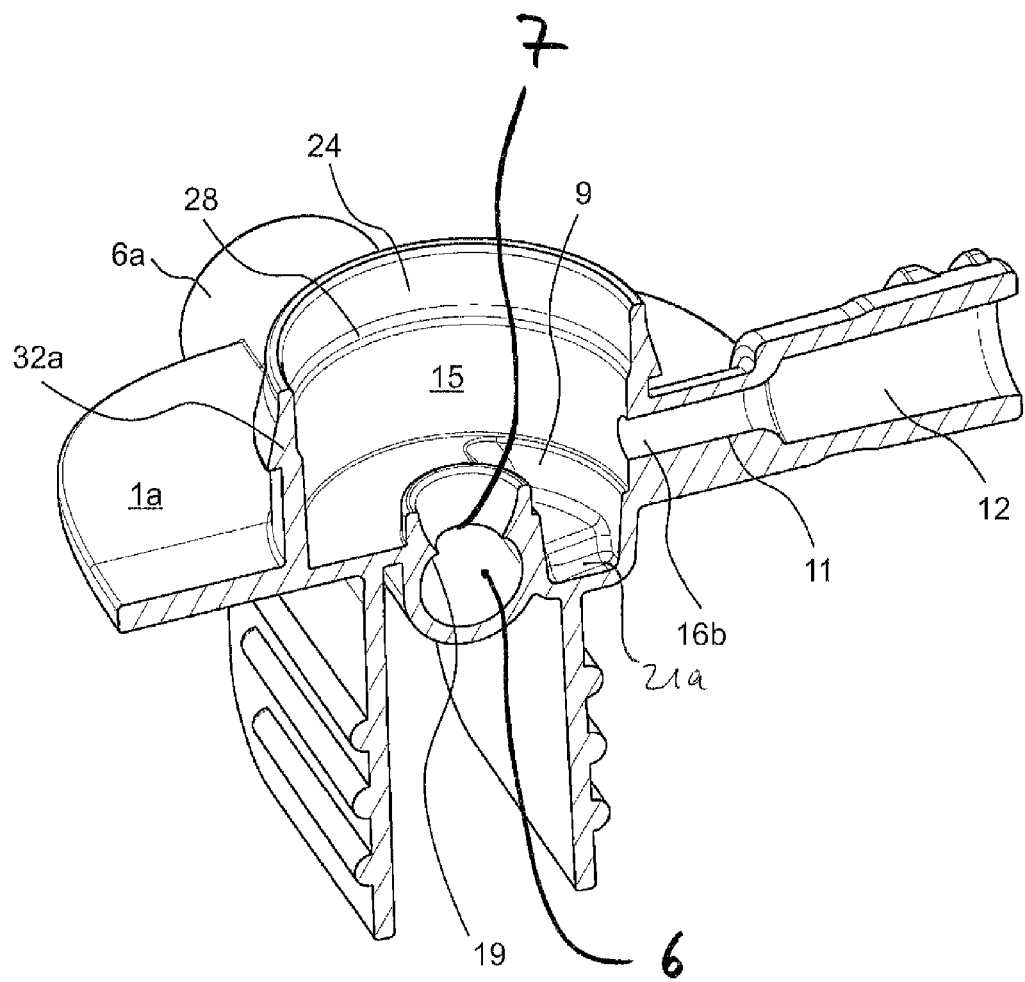
FIG. 10 shows the housing element of a further exemplary embodiment in a longitudinal section through the secondary channel, again in perspective view.

FIG. 10 shows the housing element 1 in a further exemplary embodiment in a longitudinal section through the secondary channel, again in perspective view.

The secondary channel tube 11 is in fluid connection with the main channel 6 via a secondary channel bore 16b of the switch cup 15 of a further exemplary embodiment.

As shown in FIG. 10, the main channel 6 in the area of the septum bore 7—and/or in the area of the secondary channel bore 8, although not shown here—can advantageously also comprise a flattened inner form 17. Additionally or alternatively to this, the main channel 6 can comprise a form change 19 or a transition from flat to the essentially cylindrical form of the circumference of the lumen cross-section.

In certain exemplary embodiments according to the present invention, the septum bore 7 and/or the secondary channel bore 8 are each arranged to each approximately the same part in the area of the flattened main channel form and in the area of the cylindrical main channel form. The septum bore 7 or the secondary channel bore 8 intersect thus the more closely rounded edge formed by the concurrence of the curved or cylindrical sections of the main channel cross-section with its flattened or straight sections. Thus, with reference to the secondary channel bore 8, it is advantageously possible by turning the seal element 2 on the one hand, to release or close a sufficiently large opening cross-section of the secondary channel bore 8, whereby for this only a small rotary movement is required. On the other hand, the housing element 1 and the seal element 2 contact each other only slightly in the area of the sealed bore hole walls; they have only a small rotary contact with one another. This minimizes or prevents problematic dynamic friction and from that as the case may be, a resulting reduced seal pressure and/or a falling behind of the sections of the seal element 2 which seal the openings of the main channel 6 relative to the nominal switching angle, or it completely prevents this.

Figure 10A:
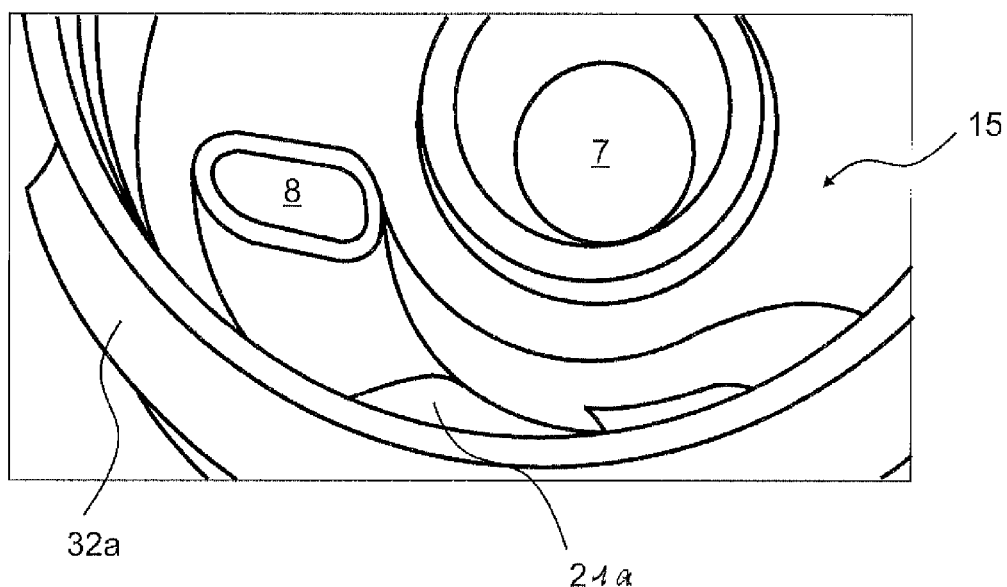
FIG. 10a shows an angled view from above in a cutaway of the switch cup with a recess for a sealing nose.

FIG. 10a shows in an angled view from above, in a cutaway of the switch cup 15, a recess 21a in the secondary channel 9, in which a sealing nose 21 (see FIGS. 12 and 13) can be turned.

Figure 11A:
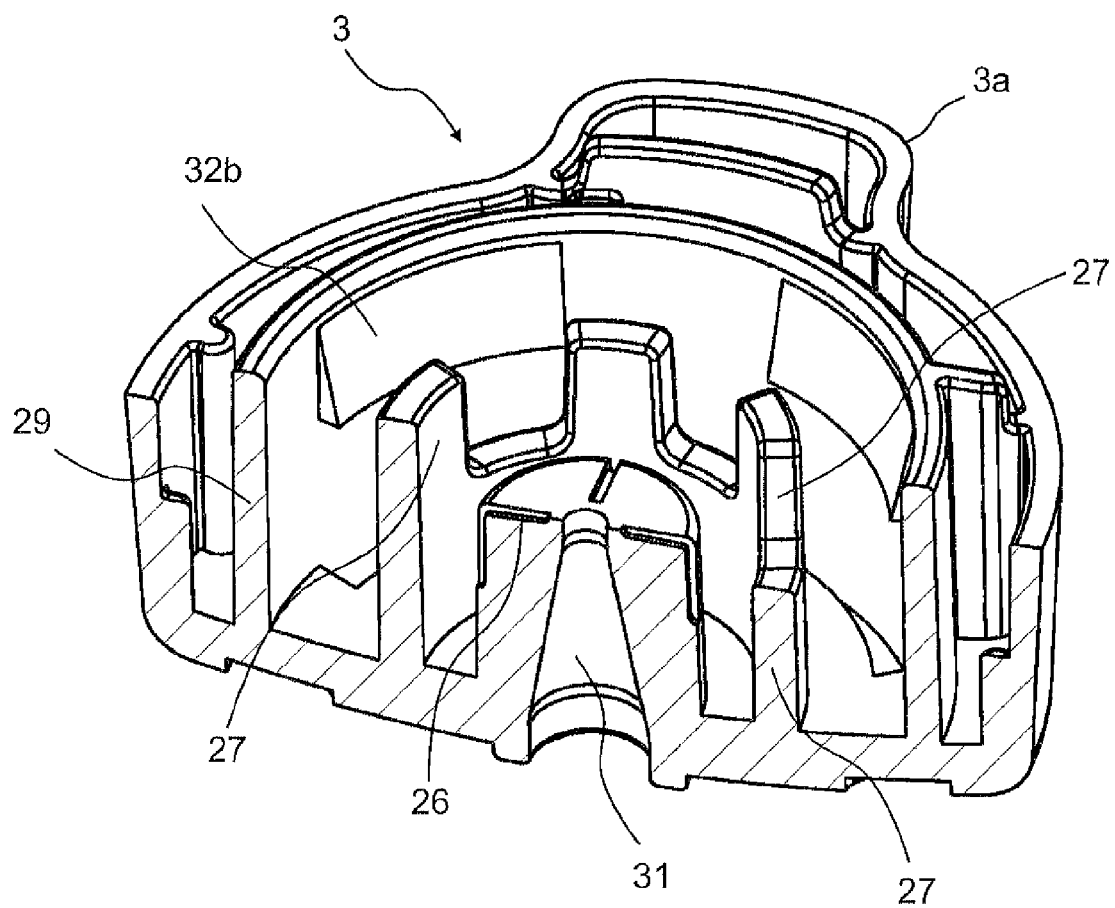
FIG. 11a shows a cross-section of the underside of the actuation element of a port according to the present invention in perspective view.

FIG. 11a shows the underside of actuation element 3 in a further exemplary embodiment in a cross section through the insertion channel 31, again in a perspective view.

To guarantee the contact protection of the surface of the septum 7a, this is only accessible through an insertion channel 31. The insertion channel 31 can according to FIG. 11a be designed to be so narrow that even with the maximum tipping of the axis of the cannula 42 against the axis of the insertion channel 31, it is not possible to pierce into material areas of the housing element 1 which are located around the septum bore 7 and which limit the main channel 6, with the tip of the cannula 42. For this reason, piercing the septum 7a is particularly ergonomic and possible with high security from contamination of the fluid of the main channel 6 through material detachment and spreading by means of cannula 42. The access to the surface of the septum 7a using spray disinfecting media remains assured.

The actuation element 3 comprises additionally elements 26 which are designed as bars and slots. These benefit the sterilizability and the compressibility; furthermore, they support.

Furthermore, the rotation carriers 27 designed as forks and pockets can again be seen in FIG. 11a.

Figure 11B:
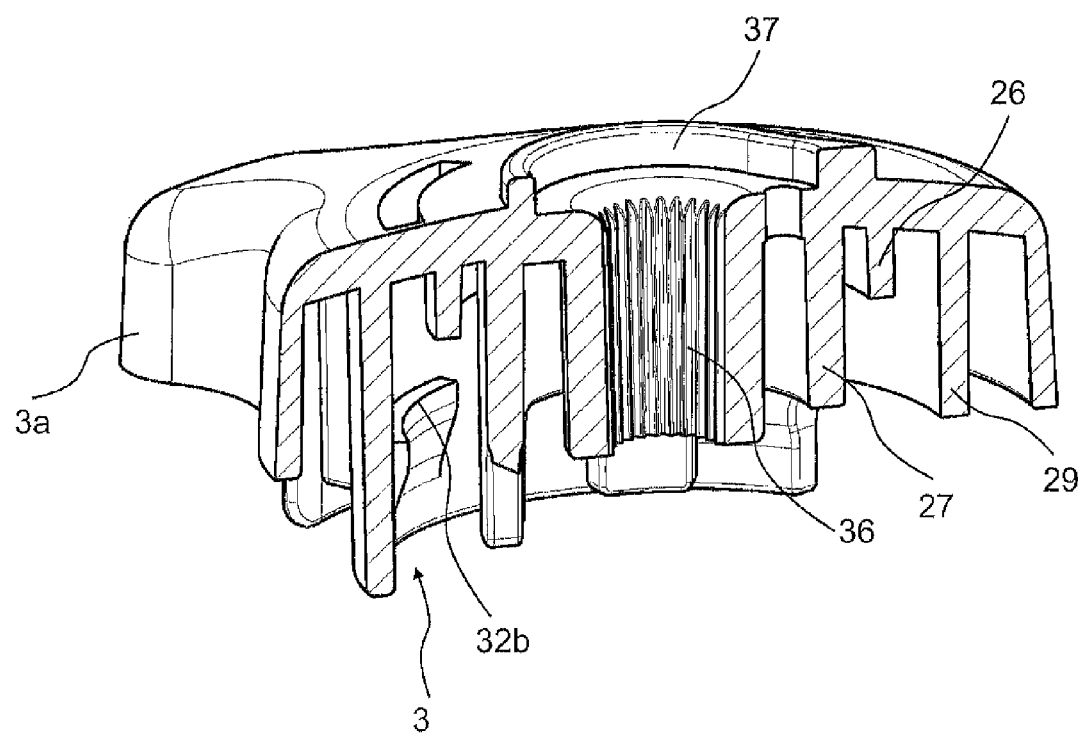
FIG. 11b shows the actuation element of yet a further exemplary embodiment of the port in cross-section, again in perspective view looking on the upside.

FIG. 11b shows a further exemplary embodiment of actuation element 3 in a cross-section through the insertion channel 31 again in perspective illustration, with a view on the upside.

To accelerate drying or re-drying of the surface of the septum 7a after sterilization by means of a fluid, the inner wall of the insertion channel 31 comprises in some exemplary embodiments according to the present invention a groove structure 36 as shown in FIG. 11b. The groove structure 36 can reach up to the surface of the septum 7a. The grooves of the groove structure 36 are formed with sufficient depth and close enough to one another with numerous recesses, indentations or capillaries to intake a liquid disinfectant (for example through adhesion) and to drain this off in the direction of the open egress of the insertion channel 31 again. Thus, there is both a fast thinning and/or distribution of the liquid disinfectant on the septum 7a as well as an accelerated evaporation due to the surface area increase achieved.

Furthermore, the insertion channel 31 can advantageously be constructed such that it opens out towards both sides. The insertion channel 31 can be funnel-shaped. Its narrowest point is facing towards the surface of the septum 7a. In some exemplary embodiments according to the present invention, the narrowest point is positioned approximately the length of a cannula blade away from the surface of the septum 7a. While the widening in the area of the insertion opening serves to ease the insertion of the cannula 42 into the opening, the second—usually smaller—widening at the other end of the insertion channel 31 should prevent a chip or particle be detached by the cannula 42 from the wall of the insertion channel 31 which could be displaced with the tip of the cannula 42 through the septum 7a into the main channel 6. The tip of the cannula 42 thus reaches the outside once again after passing through the narrowest point. This reduces the probability that the tip of the cannula 42 will pierce the circular border between the surface of the septum 7a and the wall of the insertion channel 31. In order that the narrow insertion channel 31 does not lead to a complicated insertion of the cannula 42, this can widen to a larger diameter; thereby, the benefits achievable with a limitation of the possible insertion angles are retained.

FIG. 11b shows a further circumferential contact protection bar 37 of a larger diameter. It also protects the opening area of the actual insertion channel 31 from contact. Prevented particularly by means of the contact protection bar 37 is a situation in which the user contacts the housing in the area of the insertion opening, misses the opening during piercing and/or contacts the unsterile areas with the cannula 42 and finally pierces through the septum 7a with the contaminated cannula 42. Thus, an infection protection is advantageously ensured even in case the operator should do without a liquid disinfection.

The port 100 is in certain exemplary embodiments according to the present invention suitable for every known method of sterilization, in particular those in which radiation, gas or steam are used.

For sterilization methods in which sterilizing fluids must reach all relevant surfaces, suitable diffusion paths between surfaces next to or in contact with each other are to be provided. As with specifics already described before, a large part of all surfaces in which the housing element 1, the seal element 2, and/or the actuation element 3 can come into contact with each other comprises numerous elevated or recessed support-, drainage-, and compressibility structures 25. Such structures are to be seen in FIG. 12a which shows the seal element 2 from the fluid contact side, and in FIG. 12b which shows the seal element 2 from the actuation element 3 side out. In certain exemplary embodiments according to the present invention, these structures 25 are at the same time sufficiently flexible, rigid, and arranged in optimized separation distance under optimized expansion clearances. Some of these bars can be curved in design. These can advantageously contribute to minimizing dynamic friction.

In some exemplary embodiments according to the present invention, the secondary channel bore 8 lies completely in the area of the flattened interior or peripheral area of the main channel 6. This exemplary embodiment is particularly suitable for a rotary movement of the seal element 2, combined with a sealing of the secondary channel bore 8 which is substantially based on axial compression forces. On one such axially sealing exemplary embodiment, the seal element 2 comprises for example an end face seal surface 20 (see FIG. 13). The end face seal surface 20 is located in the closed valve position—under an essentially constant axial load—centrally sealing or even overlapping over the secondary channel bore 8. The end face seal surface 20, when the seal element 2 by means of the actuation element 3 is turned to the open valve position, arrives in an area adjacent to the secondary channel bore 8. A section which is placed directly adjacent to the seal surface 20 and which is located in the seal element 2 of the secondary channel 10, comes to rest when the actuation element is turned to open the valve, over the secondary channel bore 8 and conducts a fluid flow to further secondary channel structures of the switch cup 15. Since the end face seal surface 20 during use in the switch cup 15 in this exemplary embodiment is arranged to ensure a constant seal pressure fundamentally even and vertical to the rotary actuation axis, in such exemplary embodiments the main channel 6 is also most flattened at the location of the secondary channel bore 8. Thus, the possibility exists to provide a smooth thin wall between the main channel 6 and the end face of the switch cup 15. The wall thickness is in some exemplary embodiments according to the present invention approximately only a maximum of 10% of the main channel diameter. Thereby in the closed valve position a correspondingly small blind hole is formed at the main channel 6, advantageously avoiding dead space.

Figure 13:
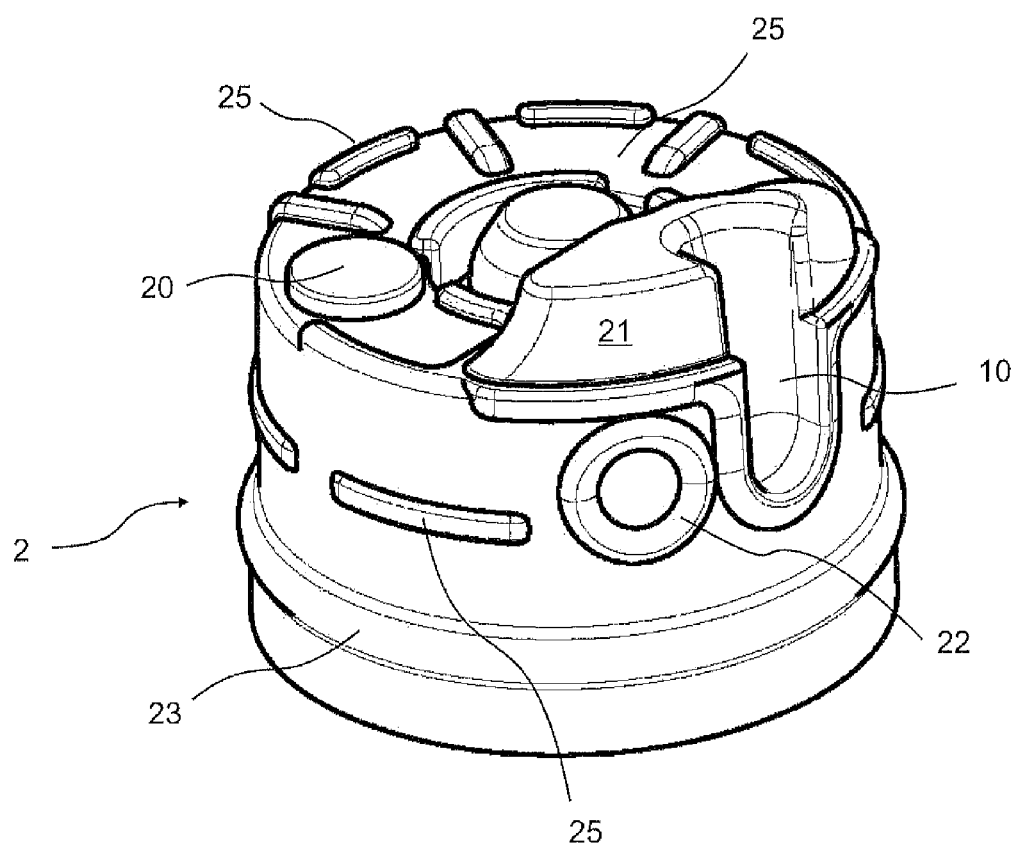
FIG. 13 shows a further exemplary embodiment of the seal element in perspective view.

In certain exemplary embodiments according to the present invention, for example in the first exemplary embodiment described above, the seal element 2 comprises one or more stuffing box packing rings 23, as can be seen in FIG. 13. Stuffing box packing rings 23 of the seal element 2 can lie flat on the stuffing box packing zones 24 of the switch cup 15 (see FIGS. 9 and 10). Stuffing box packing rings 23 can surround the seal element 2 in a circular form.

To increase the sealing effect, the seal element 2 can be supported and pressed in its interior in a radial direction through—for example circular—bars of the actuation element 3 and/or on its exterior through—for example circular—elements of the switch cup 15. Such bars, elements or the like are also denoted as support structures in the following.

In some figures and first and foremost in FIG. 10, it is to be seen that the switch cup 15, in addition to its cylindrical internal area which likewise supports the seal element 2, comprises a further support structure in the form of a—for example stepped—area 28. The stepped area 28 comprises a section with a more or less conical or tapered cross-section or a circumferential step. Depending on the axial arrangement of the seal element 2—referenced to how deep it is inserted into the switch cup 15—either a purely radial pressing between the purely cylindrical support structures of the switch cup 15, or a semi-axial or a purely axial seal pressure on the more or less conically or tapered designed section of the stepped area 28 may be permitted.

So that the seal element 2 does not begin to creep, because of its permanent pressing in the as yet unsupported axial spatial direction, primarily in the direction of the open end of the septum cup, the actuation element 3 preferably comprises a, for example, annular axial support rib 29. This presses on the outward facing end face of the seal element 2 and leads to an elastically acting axial preload through to the area of the stuffing box packing ring 23. Axial and radial elastic deformations come about thus, such that the total volume of the seal element 2 is not limited through the housing element 1 and/or through the actuation element 3. In fact there are areas in which the seal element 2 is in contact with liquid or gas. Thus, the seal element 2 is allowed an elastic flexible and shear movement. The particularly well balanced alternating arrangement of preload supported and unsupported areas provides a constant, fatigue free and tolerance-tolerant preloading of the stuffing box packing ring 23 and thus a permanent tightness during manufacturing assembly, sterilization, storage, and use.

The septum 7a and the sections of the seal element 2 surrounding it ensure, due to their form, the required sealing towards the septum bore 7 in the housing element 1 or the required the support of the seal element 2 against the actuation element 3. The exemplary embodiment of the closing end face 18 of the septum 7a has already been described with regard to the dead space free closing of the septum bore 7 in all positions of the actuation element 3. The cambered or tapering side faces 30 (FIG. 2a) and the assigned side faces of the seal area of the septum to the septum bore 7 which are differently cambered, are arranged rotationally symmetrical to the rotational axis of the actuation element 3. The cambered side faces 30 lead to a composite axial-radial seal manner under axial preload. By means of the different camberings of the side faces 30 with closely fitting and free zones, the above described effects of an optimum elastic preload are realised. Further advantageous effects of this design are as follows: a) it is automatically self centering during assembly, b) the free spaces are in gas-permeable connection with other free spaces through sterilization slots 25 so that the sterilization is advantageously supported through direct exchange of substances and no long diffusion paths for the sterilization medium are produced, c) additionally it produces a permanent pressure loading in the septum material which advantageously supports the re-sealing of the insertion channel after pulling out of the inserted cannula, d) too high friction torques, which are frequently caused through too large pressed elastomeric surfaces, are avoided and therewith disadvantageous actuation moments and also torsional distortion of the elastomer which through form change can lead to leakages.

The sections of the seal element 2 facing the actuation element 3 are predominantly designed such that—preferably essentially or predominantly—a full support of the seal element 2 to prevent torsion, axial displacement, and radial creep is ensured. The actuation element 3 has on its underside facing the seal element 2 for this purpose preferentially three annular ring bars which accurately fit in corresponding slots of the seal element 2, preferably even under a spatial expansion preload. The innermost ring bar forms at the same time the cannula insertion channel 31, the middle ring bar encircles at the same time the rotation carriers 27, and the outer ring bar encircles at the same time the axial support rib 29. The inner ring bar preferably comprises on its end face fine slots or bars 26, which ensure a safe sterilization of the fringe of the insertion zone of the cannula 42, without restricting the axial support.

The sealing of the secondary channel bore 8 against the main channel 6 and against the secondary channel structures is achieved in some exemplary embodiments as described in the following.

The switch cup 15 comprises—predominantly in the area of its end faces, close to the main channel 6—secondary channel structures, which are designated as secondary channel 9 of the housing element 1. They serve mainly as a fluidic connection between the secondary channel bore 8 in the main channel 6 and the secondary channel bore 16 in the switch cup 15 (see FIG. 10).

Depending on embodiment and switch position, the structures of the secondary channel 9 in the housing element 1 with the assigned structures of the secondary channel 10 of the seal element 2 can complement each other. Together, the structures of the secondary channel 9 and the structure of secondary channel 10 conduct the fluid that makes up the secondary channel flow 14.

Furthermore, in some exemplary embodiments according to the present invention, the walls of the secondary channels 9 and 10, in particular in direct proximity to the bores to the main channel 6, form one or more sealing seats of the seal element 2. Due to their shape and the shape of the seal elements 2, these structures permit for example rotation of the seal element 2, which is with at least one end position angularly limited. Thereby, it can come to a seal in the end position of rotation or, as the case may be, to a dead space free closure of the septum bore 7 and/or the secondary channel bore 8 against the main channel 6.

Also in arbitrary intermediate positions, which the sealing element 2 in its rotation within the housing element 1 can take, the essentially cylindrical wall structures together with the stuffing box packing ring 23 of the seal element 2 (see FIG. 12a or 13) and the stuffing box packing zone 24 of the switch cup 15 (see FIG. 10) provide for a permanent outward fluid sealing.

To permit switching movements and simultaneously in doing so avoid dead space as far as possible, for example a sealing nose 21 (FIG. 12a) of the seal element 2 in certain exemplary embodiments of the present invention is arranged. This can be moved in the transition from the closed to the open valve position, exemplarily in a rotary movement or on a turning radius around a fulcrum. In some of these exemplary embodiments, a free minimum space or a recess 21a in the housing element 1, see FIG. 10a, to accommodate the sealing nose 21 is provided. The free minimum space is provided in some exemplary embodiments of the present invention due to the design of the secondary channel 9 in the switch cup 15, as can be seen in the designs of FIGS. 9, 10 and 10a.

Depending upon the spatial position of the secondary channel bore 8 in the switch cup 15, see FIGS. 9 and 10 for variants, and depending upon the width of the rotary or switching angle range of the actuation element 3 and the arrangement of the secondary channel bore 8 to the main channel 6, radial and axial structures of both the secondary channel 9 of the housing element 1 and the secondary channel 10 of the sealing element 2 can be designed to be different, and above all different in length. Thus, the seal element 2 comprises according to FIG. 12a predominantly structures of the secondary channel 10 which are designed radially to the seal element 2, whereas the secondary channel 10 of the seal element 2 according to FIG. 13 comprises predominantly axial structures with reference to the seal element 2.

Figure 12A:
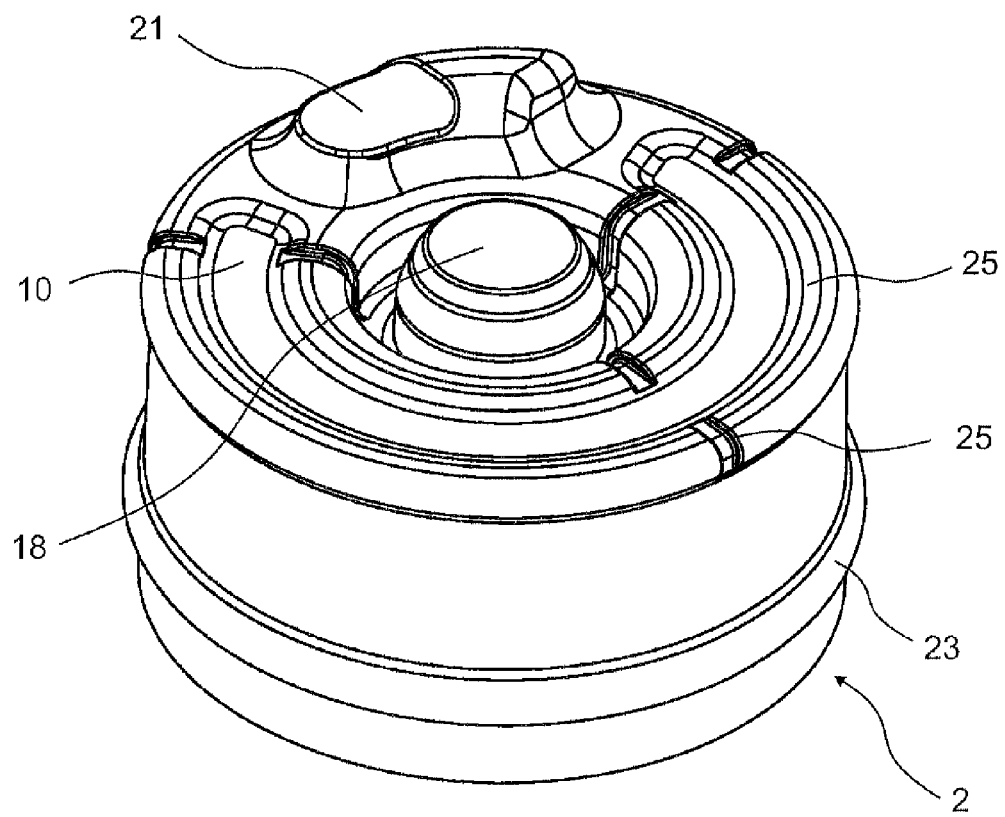
FIG. 12a shows the seal element of a port according to the present invention viewed from the fluid side, in slightly perspective view.
Figure 12B:
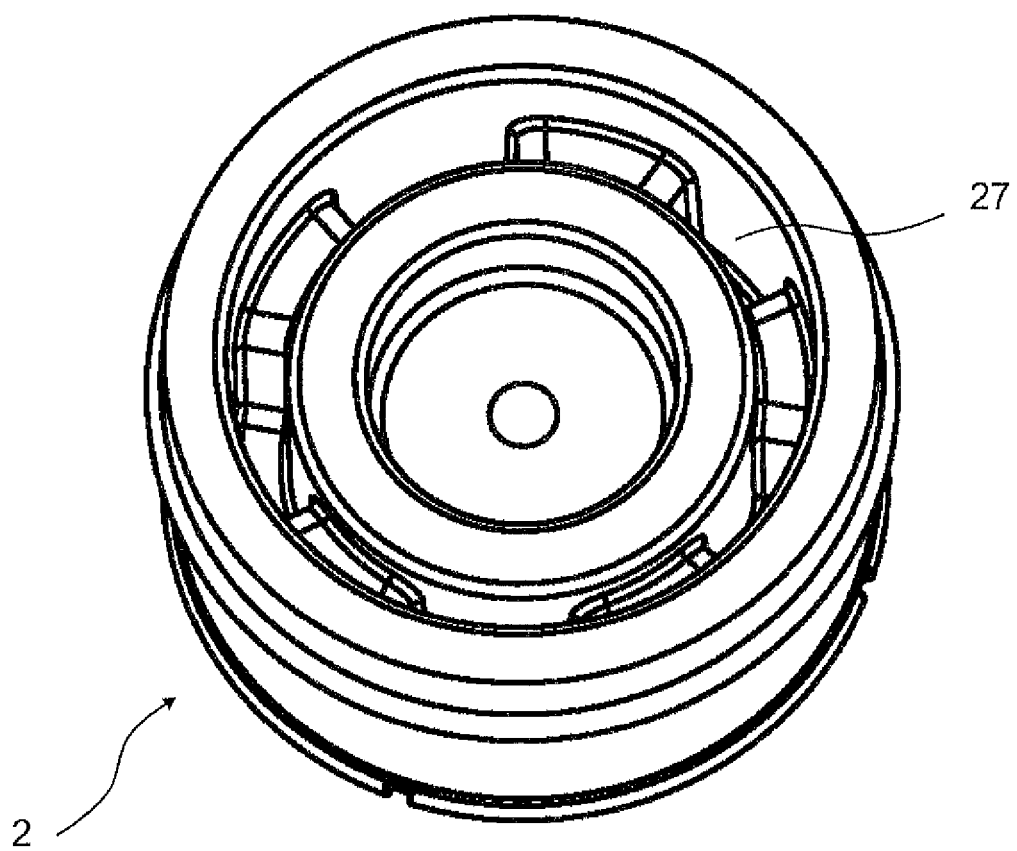
FIG. 12b shows the seal element of FIG. 12a viewed from the side of the actuation element.

The designs of the housing element 1 according to FIG. 9 and the seal element 2 according to FIG. 12a comprise jointly only one switchable seal or block of the secondary channel flow 14 against the main channel flow 13. This takes place at the transition of the secondary channel bore 8 to the main channel 6. The switchable arrangement advantageously enables a dead space free sealing of the secondary channel tube 11 directly—or in the area of secondary channel bore 8—at the main channel 6. The switchable arrangement permits in addition that all secondary channel spaces in the closed valve position are accessible to sterilization gases through a secondary channel connector 12 covered with an open (contact-) protective cap 5 and the secondary channel tube 11. Compared with conventional switching of the secondary channel 8 to the main channel 6, for example by means of opening or closing a hose clamp, the advantage arises that both sterilization by means of steam or gas in general as well as a permanent storage of the port 100 respectively (at least also) is possible in the closed valve position until the usage of the port 100. For this reason, the danger that the addition point or the addition valve, i.e., the connection from the secondary channel to the main channel 6, is opened for sterilizing the port 100, and then, however, at or ahead of the usage of the port 100 is inadvertently not closed again, is advantageously reduced.

Figure 14A:
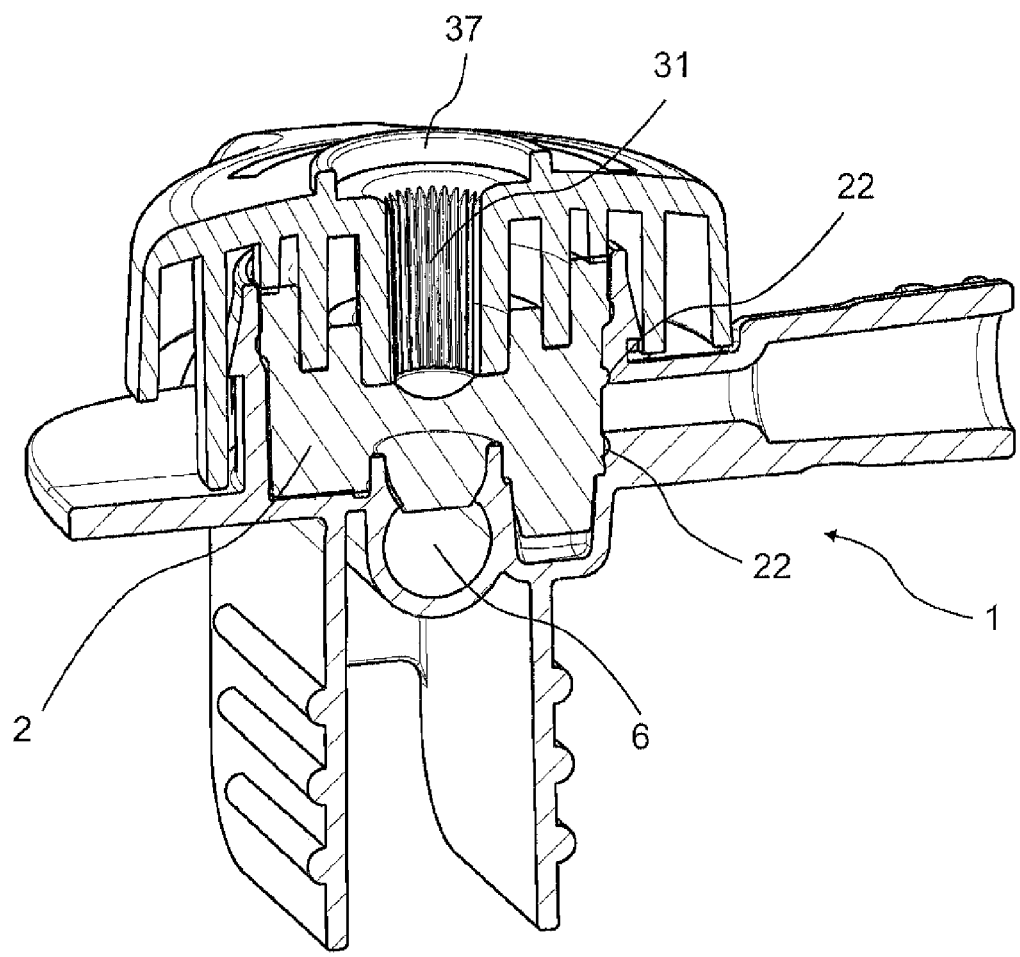
FIG. 14a shows an exemplary embodiment according to the present invention of the port viewed in a frontal section in the closed valve position and with double sealing.
Figure 14B:
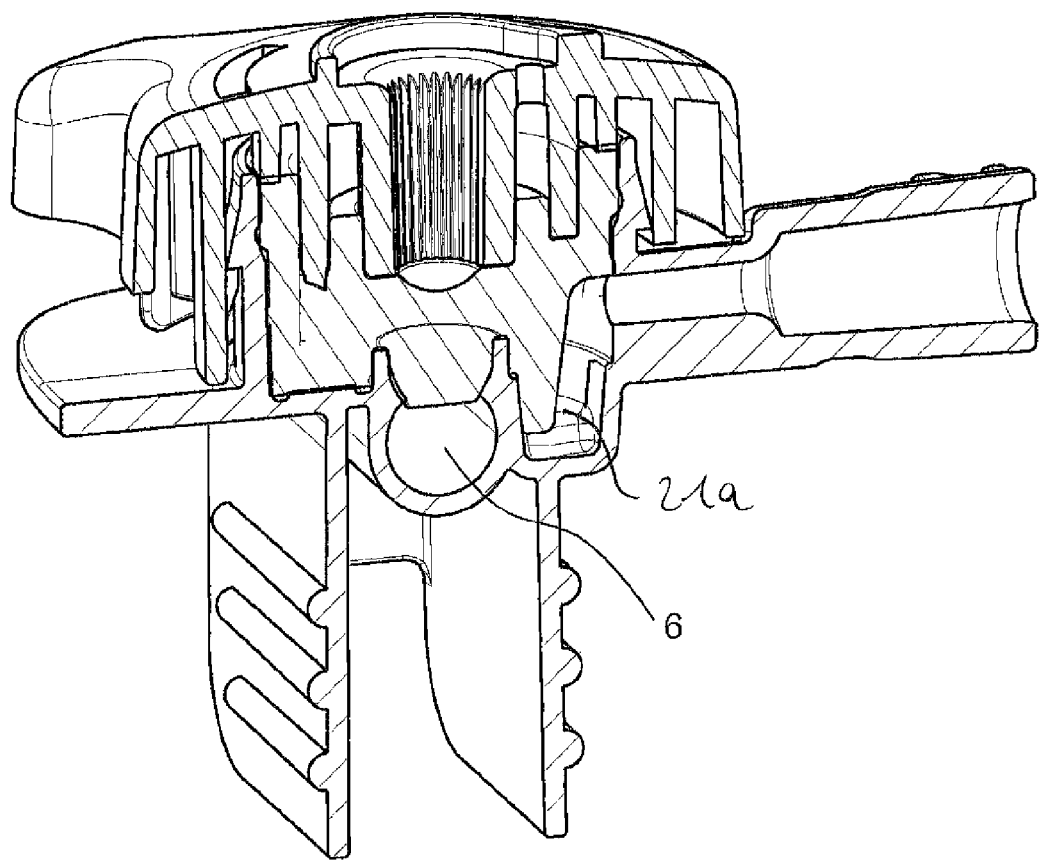
FIG. 14b shows the port of FIG. 14a in the open valve position.

FIGS. 14a and 14b show a section through a port 100 of a further exemplary embodiment according to the present invention, with a switch cup 15 already shown in FIGS. 10 and 10a. In this exemplary embodiment, the port 100 in the switch cup 15 has available an additional sealing option (also designated as secondary seal or double seal) of the main channel 6 against the secondary channel bore 8.

The seal element 2 comprises in this exemplary embodiment, for example, on its outer shell surface, an elevated radial seal structure 22, which for example in a circumferential or closed or annular design is shown in FIG. 13. Differing from this, the radial seal structure 22 can of course also be round or of elongated hole shape. The latter can advantageously contribute to increasing a tolerance against incorrectly executed switching angles, or vice versa, such that the requirements for the production tolerance can be reduced.

The radial seal structure 22 can comprise a radially rising external surface, which is based upon or complementarily suits the curved inner surface in the circumferential direction of the cylindrical form of the switch cup 15.

Through the radial seal structure 22 under assembly preload, a thin closed or annular close fitting pressed zone around the secondary channel bore 8 in the switch cup 15 can be produced. Through this, an additional, second sealing against the inside of the secondary channel tube 11 can be achieved.

Advantageously, the requirements for the tolerances of the components of the above described first seal structure can be reduced. At the same time, this exemplary embodiment can advantageously increase the seal effect.

The design with secondary seal or double seal, as a double sealing of the secondary channel against the main channel 6, comprises advantages in certain exemplary embodiments according to the present invention, such as for example, that one or both sealings are predominantly or fully axially (com) pressed seals, which by increasing the pressure difference between the separate fluid spaces are in one pressure direction self-reinforcing, in the other pressure direction though under a preload reduction effective. There can be thus a limiting pressure in the respective unfavourable pressure direction at which the preload is nullified and the sealing is lifted. Both seals are now however, relative to their direction of action, arranged inversely. It can hereby be alluded to as a bi-directional seal reinforcement. Thus, at least one of the seals can experience a self-reinforcement through which very high seal limiting pressures up to the destruction limit of the housing can be reached.

In some exemplary embodiments according to the present invention, the sealing zone at the secondary channel bore 8 to the main channel 6 comprises a structure which as a capillary or through slightly mismatched or inconsistent geometries between the housing element 1 and the seal element 2 creates an unsealed position. Nonetheless, at the main channel 6 there is no dead space in relation to the desired flow conditions. Thus, the particularly high sealing effect of the secondary channel seal on the switch cup 15, the good gas sterilization properties of the port 100 and the freedom from dead space in the main channel 6 can be combined.

As in many cases before the start of treatment, e.g., the dialysis, the main channel 6 is flushed and filled, one can let the fluid used for this permeate already into the secondary fluid structures and at least partly dissipate or flush out air pockets present there without the valve having to be opened for this purpose.

Figure 15A:
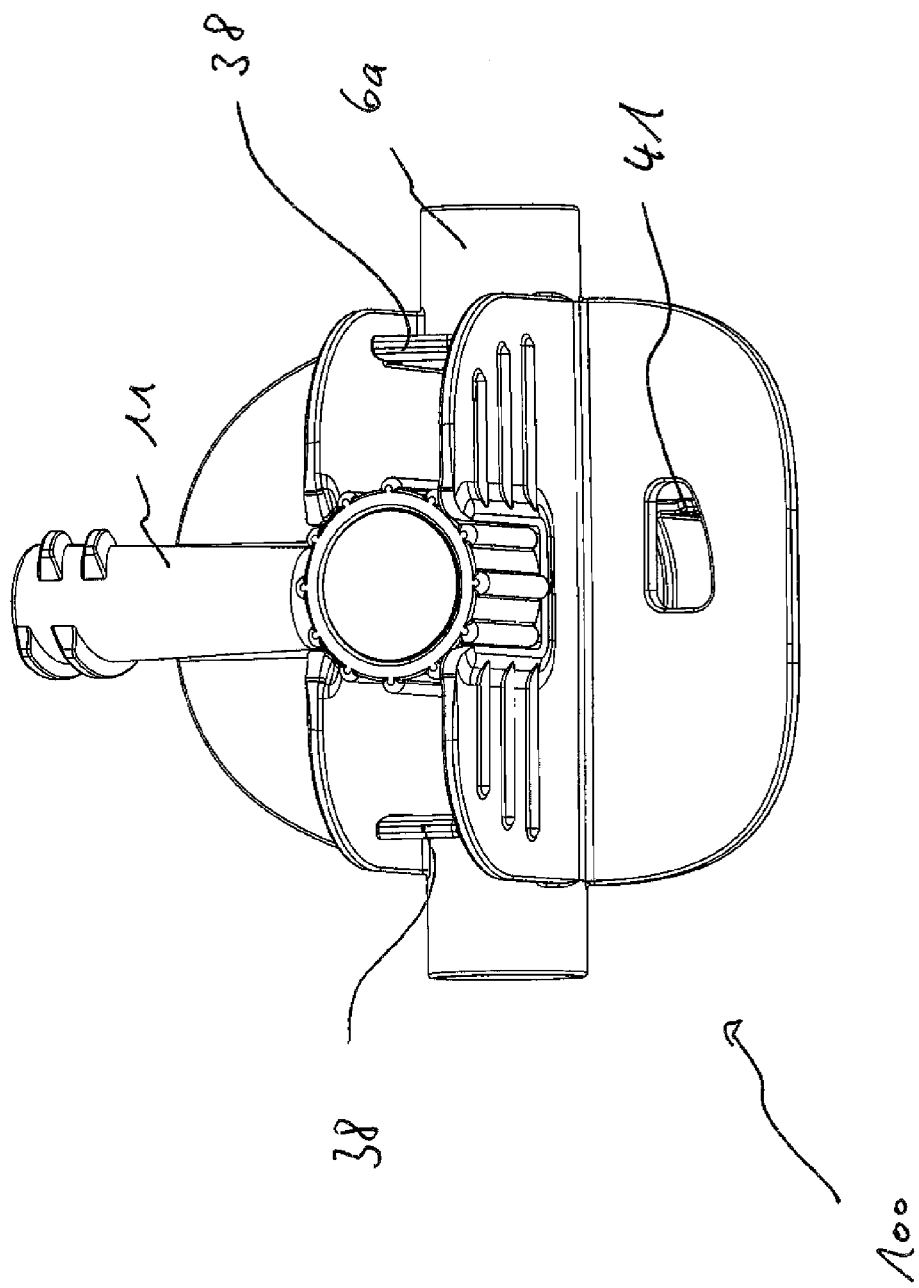
FIG. 15a shows a further exemplary embodiment of a port according to the present invention in the closed valve position.

FIGS. 15a and 15b show a further exemplary embodiment of the port 100 according to the present invention with a device to monitor the switching position or the position of the actuation element 3. The device to monitor the switching position interacts with tactile and/or optical sensors on the machine base. In the piercing protection plate 1a or in another section of the housing element 1 is preferably located an aperture 40, which is for example essentially of elongated hole shape, through which a contact with a switch cam 41 for its tactile check or an optical perceptibility of the switch cam 41 is ensured. The switch cam 41 can be arranged in the machine base in such a way that it is accessible for a monitoring by means of sensors. By means of a suitable design of the aperture 40, the switch cam 41, machine base and sensor system, a lock-key principle can additionally be established whereby not only the presence of the port 100 in the correct position on the machine base is recognized but at the same time presence manipulation is made difficult. FIG. 15a shows a state in the closed valve position, FIG. 15b shows a state in the open valve position.

In some exemplary embodiments according to the present invention, as is also shown in the Figures, already a small rotation of the actuation element 3 leads to a start of the throttle or valve effect of the port 100. Hence are provided in some exemplary embodiments according to the present invention in addition to the rotary detents, friction or fine stepped zones; in other exemplary embodiments according to the present invention, the friction or fine stepped zones replace the rotary detents. However, since the throttle characteristic curve, in particular with the otherwise unchanged design of the secondary channels 9,10 and the sealing nose 21 of the seal element 2 is not linear, in certain exemplary embodiments according to the present invention a gradually extending wedge shaped seal gap is provided as is also found in regulating valves. With this exemplary embodiment, a linearity of the throttle effect across an arbitrarily wide rotational angle range can be achieved, inside which the actuation element 3 can be rotated.

Variable restriction grades or sealing grades relative to the secondary channel bore 8 in the switch cup 15 or septum cup or in the seal element 2 are achievable by providing for example wedge-shaped radially or spirally running secondary channel structures in the seal element 2. These bring into contact differently sized cross-sections of a fluid line inside the seal element 2 with the secondary channel bore 8, depending on the adjusted angle of rotation.

In some exemplary embodiments according to the present invention, a protection against a return flow of the fluid in the in the secondary channel of the port 100 is provided. This protection prevents an outflow of liquid through the secondary channel tube 11; however, it allows at the same time under a sufficiently low pressure decrease the conveyance of secondary fluids into the main channel 6. This can be provided by means of a non-return valve with an inflow-non-return valve function. In doing so, the non-return valve is under a known preloading. It provides that the seal effect is sufficiently high to prevent air penetrating through the secondary channel tube 11 until a specific or predetermined underpressure in the main channel 6 relative to the surroundings.

In particular the above described double sealed exemplary embodiment of the port 100 according to the present invention has already, besides the open and the closed valve position, an advantageous non-return valve effect. Indeed, the valve prevents through self-reinforcement an escaping of liquids against high pressure differences; it remains possible, however, due to the resilience or compliance and the neutralization of the preload under reverse fluid pressure, to introduce liquids into the main channel 6 after overcoming a pressure limiting value. By lowering through design measures the preload of the seal to the secondary channel bore 8 in the switch cup 15, a non-return valve with an arbitrarily low adjustable cracking pressure is attained.

An obstruction of the opposite direction of flow through the non-return valve is hereby achieved, just as an undesired restriction.

To reduce the preload, various possibilities are provided according to the present invention: if the radial seal structure is for example designed as a ring form whereby the ring has a—in particular significantly—larger outer diameter than the bore in the septum cup, so the area subject to pressure in the outlet direction is clearly increased and the cracking pressure thus reduced. Likewise it is possible to design the seal element 2 in the non-return valve position radially less innately stiff and to reduce the counter support from the annular bars in the actuation element 3 through discontinuities and/or slots.

By means of the last mentioned exemplary embodiment, the port 100 according to the present invention permits, in addition to the so far discussed positions (open valve position and closed valve position), also an in-flow non-return position. In some exemplary embodiments thus, by means of the port 100 according to the present invention, both valves can be implemented with either only two switching positions, or with three locking positions and three different fluid functions. In the closed valve position, the advantage of the redundant and/or dead space free seal on the secondary channel bore 8 against the main channel 6 is always maintained.

| REFERENCE NUMERAL LIST | |
|---|---|
| Reference numeral | Description |
| 1 | housing element |
| 1a | piercing protection plate |
| 2 | seal element |
| 2a | section of the seal element |
| 3 | actuation element |
| 3a, b | knob |
| 3c | arrow |
| 4 | connecting hoses |
| 5 | protective cap |
| 6 | main channel |
| 6a | hose sleeves |
| 7 | septum bore or septum aperture |

REFERENCE NUMERAL LIST

| Reference numeral | Description |
|---|---|
| 7a | septum |
| 8 | secondary channel bore or secondary channel aperture |
| 9 | secondary channel in housing element |
| 10 | secondary channel in seal element |
| 11 | secondary channel tube |
| 12 | secondary channel connector |
| 13 | main channel flow |
| 14 | secondary channel flow |
| 15 | switch cup |
| 16a, b | secondary channel bore in switch cup (first and second exemplary embodiments respectively) |
| 17 | flattened inner form of the main channel |
| 17a | flattening of the seal element |
| 18 | closing end face of a septum seal element |
| 19 | form change edge of the main channel |
| 20 | end face seal surface of the seal element |
| 21 | sealing nose of the seal element to the main channel |
| 21a | recess |
| 22 | radial seal structure of the seal element to the secondary channel bore in the switch cup |
| 23 | stuffing box packing ring of the seal element |
| 24 | stuffing box packing zone of the switch cup |
| 25 | sterilization-, support- and compressibility bars and slots in the seal element |
| 26 | sterilization-, support- and compressibility bars and slots in the actuation element |
| 27 | rotation carrier |
| 28 | stepped area of the switch cup |
| 29 | axial support rib of the actuation element |
| 30 | cambered forms in the septum seal area |
| 31 | insertion channel |
| 32a, b | latching elements |
| 33 | rotation detent |
| 33a | locking catch |
| 33b | locking recess |
| 34 | rotation stops |
| 35 | bow ribs |
| 36 | groove structure in insertion channel |
| 37 | contact protection bar in the insertion aperture |
| 38 | snap-in tongues for fixing to a treatment machine |
| 39 | pictograms for function visualization |
| 39a | crescendo symbol |
| 40 | switch position aperture |
| 41 | switch position cam |
| 42 | cannula |

What is claimed is:

1. A medical port, comprising:
a main channel having a lumen configured to conduct a first fluid through the medical port;
a secondary channel aperture of a secondary channel configured to add a second fluid into the main channel;
at least one housing element;
at least one actuation element arranged relative to the at least one housing element and transferable from a first position to a second position; and
a seal section which is arranged to be rotatable between a first position of the seal section in which the seal section does not one of close, seal and cover the secondary channel aperture, and a second position of the seal section in which the seal section one of closes, seals and covers the secondary channel aperture, when transferring the at least one actuation element from the first position to the second position, wherein the seal section comprises at least one pierceable septum,
wherein the main channel is a tube,
wherein the seal section comprises a sealing nose which protrudes in an axial direction of the seal section over the seal section, wherein the sealing nose is arranged to be moved on a turning radius from a first position to a second position on the turning radius when the at least one actuation element is one of turned and transferred from the first position to the second position, wherein the sealing nose in the first position does not one of close, seal and cover the secondary channel aperture, and wherein the sealing nose in the second position one of closes, seals and covers the secondary channel aperture.

2. The port according to claim 1, wherein the seal section is arranged and designed such that a passage of the main channel for the first fluid is not impaired in the first position and the second position.

3. The port according to claim 1, wherein no section of the seal section is present in the lumen of the main channel.

4. The port according to claim 1, wherein in addition to the secondary channel aperture, the main channel comprises a septum aperture, which during use of the port is closed by a septum which is pierceable by a cannula.

5. The port according to claim 4, wherein at least one of the secondary channel aperture and the septum aperture lead into one of a straight section of a cross-section of the lumen, its periphery and a circumference of the main channel.

6. The port according to claim 1, wherein the seal section comprises a seal surface on a front, which is arranged for being moved along the turning radius from the first position into the second position on the turning radius, when the seal section is turned, wherein the seal surface in the second position one of closes, seals and covers the secondary channel aperture, wherein the seal surface in the first position does not one of close, seal and cover the secondary channel aperture, and wherein the seal surface extends at least one of in parallel to a main cross-section plane and perpendicular to a rotational axis of the seal section.

7. The port according to claim 1, wherein the at least one housing element comprises at least one section, which comprises a recess to intake the movable sealing nose, and which one of comprises and adjoins the secondary channel aperture.

8. The port according to claim 1, wherein the sealing nose comprises a groove which is open both to a front of the sealing nose and to one of a lateral side surface and a peripheral surface of the seal section.

9. The port according to claim 8, wherein in the first position of the seal section, the groove fits against an opening in a secondary channel tube such that the groove continues a fluid path of the secondary channel tube across the seal section, and wherein in the second position of the seal section, the groove is not in fluid connection with one of the secondary channel tube and its opening.

10. The port according to claim 6, wherein the seal section, in addition to one of the seal surface on the front and the sealing nose, comprises an elevated, closed seal structure which in the second position of the seal section one of (i) one of closes and seals an opening of a secondary channel tube and (ii) prevents an escape of fluid from the opening.

11. The port according to claim 1, wherein the seal section is designed as a separate seal element.

12. The port according to claim 4, wherein both the septum aperture and a secondary channel bore are arranged together in a cross-section half of the main channel.

13. The port according to claim 1, further comprising:
an intake configured to temporarily one of intake and fix a protective cap, provided for covering one of a secondary channel tube and a secondary channel connector, at the port.

14. The port according to claim 1, further comprising:
an intake or fixing device configured to temporarily one of intake and fix the port at a front of a treatment apparatus.

15. A blood hose for use in an extracorporeal blood treatment, comprising at least one arterial patient line and at least one venous patient line, the blood hose comprising:
   at least one port according to claim 1.

16. The blood hose according to claim 15, wherein the port is inserted in the arterial patient line.

17. A medical treatment apparatus, which is connected with the blood hose according to claim 15.

18. The medical treatment apparatus according to claim 17, comprising:
   an intake configured to temporarily one of intake and fix the port according to claim 1 at a front thereof.

19. The medical treatment apparatus according to claim 17, comprising:
   a device configured to recognize at least one of a presence and a valve position of the port according to claim 1.

20. The medical treatment apparatus according to claim 17, wherein the apparatus is embodied as one of a blood treatment apparatus, an apparatus for apheresis, an apparatus for dialysis, an apparatus for hemodialysis, an apparatus for hemofiltration, and an apparatus for hemodiafiltration.

\* \* \* \* \*